US012586179B1

(12) United States Patent
Irani

(10) Patent No.: US 12,586,179 B1
(45) Date of Patent: **\*Mar. 24, 2026**

(54) PHYSICIAN-GUIDED MACHINE LEARNING SYSTEM FOR ASSESSING MEDICAL IMAGES TO FACILITATE LOCATING OF A HISTORICAL TWIN

(71) Applicant: Neville Irani, Stillwell, KS (US)

(72) Inventor: Neville Irani, Stillwell, KS (US)

( \* ) Notice: Subject to any disclaimer, the term of this patent is extended or adjusted under 35 U.S.C. 154(b) by 1040 days.

This patent is subject to a terminal disclaimer.

(21) Appl. No.: 17/644,975

(22) Filed: Dec. 17, 2021

Related U.S. Application Data

(63) Continuation-in-part of application No. 17/202,913, filed on Mar. 16, 2021, now Pat. No. 11,205,520.

(51) Int. Cl.
| | |
|---|---|
| *G06T 7/00* | (2017.01) |
| *G06F 16/532* | (2019.01) |
| *G06F 40/247* | (2020.01) |
| *G16H 30/20* | (2018.01) |
| *G16H 30/40* | (2018.01) |
| G06F 3/04847 | (2022.01) |

(52) U.S. Cl.
CPC .......... *G06T 7/0012* (2013.01); *G06F 16/532* (2019.01); *G06F 40/247* (2020.01); *G16H 30/20* (2018.01); *G16H 30/40* (2018.01); *G06F 3/04847* (2013.01); *G06T 2200/24* (2013.01); *G06T 2207/20104* (2013.01); *G06T 2207/30016* (2013.01)

(58) Field of Classification Search
None
See application file for complete search history.

(56) References Cited

U.S. PATENT DOCUMENTS

| | | | | |
|---|---|---|---|---|
| 7,593,967 | B2 * | 9/2009 | Harnsberger | ......... G06F 40/166 |
| 8,953,858 | B2 * | 2/2015 | Becker | ................. G06K 9/6201 |
| | | | | 382/128 |
| 10,748,661 | B2 * | 8/2020 | Takata | ................... G16H 50/70 |
| 2003/0013951 | A1 * | 1/2003 | Stefanescu | ............. G16H 50/50 |
| | | | | 600/407 |

(Continued)

OTHER PUBLICATIONS

Ian Pan, Improving Automated Pediatric Bone Age Estimation Using Ensembles of Models from the 2017 RSNA Machine Learning Challenge, Radiology: Artificial Intelligence, 2019, 9 pages, vol. 1: No. 6, radiology-ai.rsna.org, Rhode Island, USA.

*Primary Examiner* — Nancy Bitar
(74) *Attorney, Agent, or Firm* — AVEK IP, LLC

(57) ABSTRACT

A computer-implemented method of evaluating a user image of a patient to enable identification of a historical twin of the patient. The method includes organizing a plurality of medical images in an archive and receiving from a medical professional each of: (i) a region of interest; (ii) a textual description; (iii) selections for binary criteria; and (iv) weights of weighable criteria. The method comprises using a natural language search to create a relevant set of medical images and creating an optimal set from the relevant set of medical images by discarding medical images from the relevant set based at least on the selections for binary criteria. The method includes image processing medical images in the optimal set using the weight of the features of the region of interest to create medical image results. The relevant set comprises less than ten percent of the medical images in the archive.

20 Claims, 20 Drawing Sheets

(56)     References Cited

U.S. PATENT DOCUMENTS

| | | | |
|---|---|---|---|
| 2008/0095418 A1* | 4/2008 | Moriya ................. | G16H 50/70 |
| | | | 382/128 |
| 2012/0191793 A1* | 7/2012 | Jakobovits ............. | G06F 16/51 |
| | | | 709/206 |
| 2016/0350919 A1* | 12/2016 | Steigauf ............... | G06K 9/6263 |
| 2017/0091574 A1* | 3/2017 | Udupa ..................... | G06T 7/11 |
| 2019/0057778 A1 | 2/2019 | Porter et al. | |
| 2019/0371439 A1* | 12/2019 | Lisowska ................ | G06N 3/08 |
| 2020/0311467 A1* | 10/2020 | Srivastava ........... | G06N 3/0454 |
| 2020/0380027 A1* | 12/2020 | Aggarwal ............ | G06F 16/538 |
| 2021/0042878 A1 | 2/2021 | Ghose et al. | |

* cited by examiner

132

STRUCTURE 202

MEMORY 210

ANATOMICALLY
ARRANGED
ARCHIVE
220

| BIN 223A | BIN 223B | BIN 223N |
| BIN 224A | BIN 224B | BIN 224N |
| BIN 225A | BIN 225B | BIN 225N |
| BIN 226A | BIN 226B | BIN 226N |
| BIN 227A | BIN 227B | BIN 227N |

MACHINE
LEARNING
MODELS
230

API 212

PHYISICIAN-ASSISTING
SOFTWARE 240

ARCHIVER 250

METADATA
EXAMINER 251

AI ARRANGER
KEYS 252

| XRAY 253 | MRI 254 |
| CT 255 | PET 256 |

UL-S 257

IMAGE
EVALUATOR 258

HISTORICAL TWIN CIRCUMSCRIBER
260

ANATOMY DETERMINER 262

BENCHMARK APPLICATOR 264

MODEL SELECTOR 266

IMAGE PROCESSOR 268

ORGANIZER 270

REBALANCER 272

API 214

N/W INTERFACE 208          PROCESSOR 206

Metadata 608

Age: 25
Modality: MRI
Contrast: Yes
Plane: Axial
Gender: M

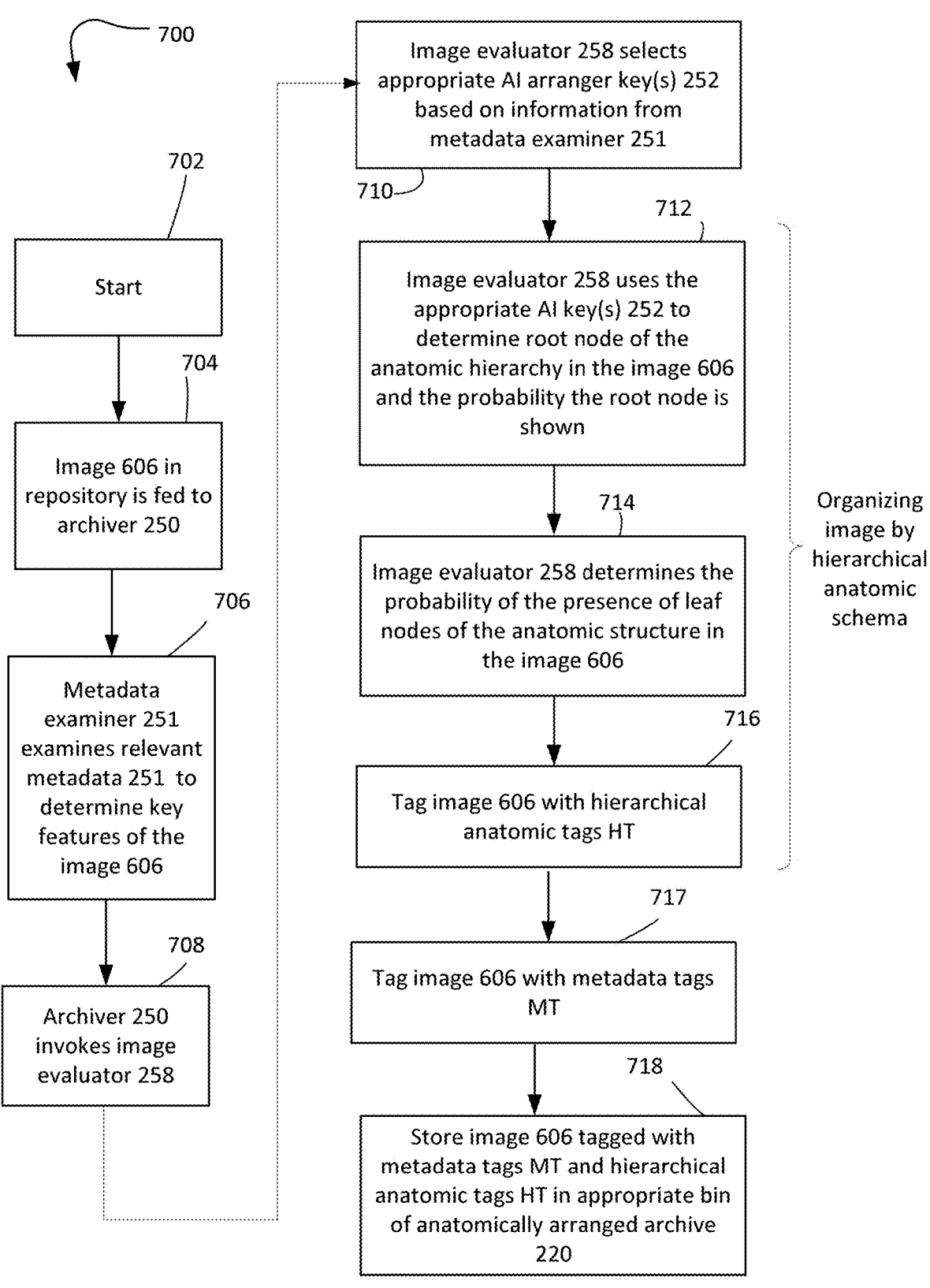

700

702

Start

704

Image 606 in repository is fed to archiver 250

706

Metadata examiner 251 examines relevant metadata 251 to determine key features of the image 606

708

Archiver 250 invokes image evaluator 258

710

Image evaluator 258 selects appropriate AI arranger key(s) 252 based on information from metadata examiner 251

712

Image evaluator 258 uses the appropriate AI key(s) 252 to determine root node of the anatomic hierarchy in the image 606 and the probability the root node is shown

714

Image evaluator 258 determines the probability of the presence of leaf nodes of the anatomic structure in the image 606

716

Tag image 606 with hierarchical anatomic tags HT

717

Tag image 606 with metadata tags MT

718

Store image 606 tagged with metadata tags MT and hierarchical anatomic tags HT in appropriate bin of anatomically arranged archive 220

Organizing image by hierarchical anatomic schema

FIG. 7

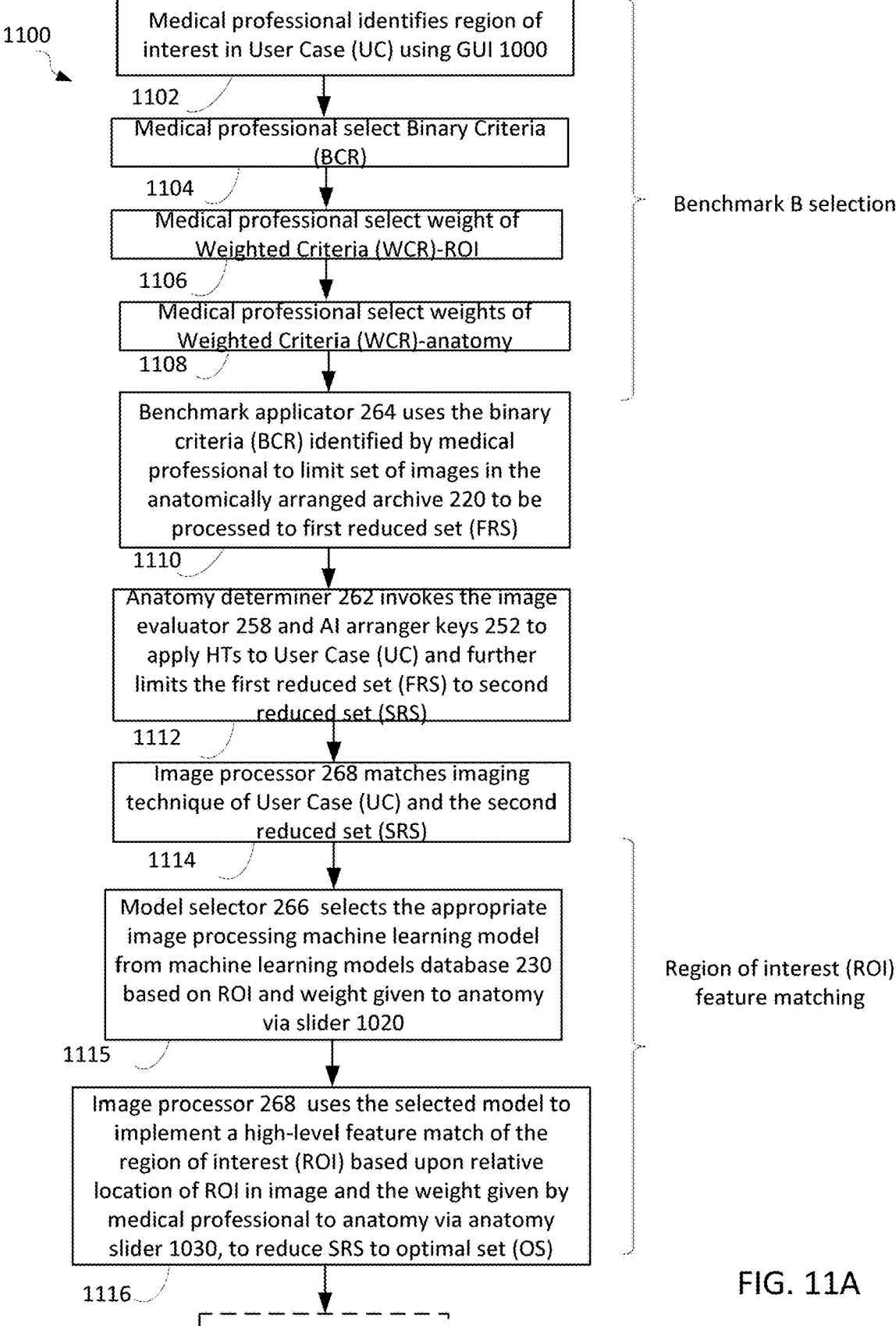

1100

Medical professional identifies region of interest in User Case (UC) using GUI 1000

1102

Medical professional select Binary Criteria (BCR)

1104

Medical professional select weight of Weighted Criteria (WCR)-ROI

1106

Medical professional select weights of Weighted Criteria (WCR)-anatomy

1108

Benchmark B selection

Benchmark applicator 264 uses the binary criteria (BCR) identified by medical professional to limit set of images in the anatomically arranged archive 220 to be processed to first reduced set (FRS)

1110

Anatomy determiner 262 invokes the image evaluator 258 and AI arranger keys 252 to apply HTs to User Case (UC) and further limits the first reduced set (FRS) to second reduced set (SRS)

1112

Image processor 268 matches imaging technique of User Case (UC) and the second reduced set (SRS)

1114

Model selector 266 selects the appropriate image processing machine learning model from machine learning models database 230 based on ROI and weight given to anatomy via slider 1020

1115

Region of interest (ROI) feature matching

Image processor 268 uses the selected model to implement a high-level feature match of the region of interest (ROI) based upon relative location of ROI in image and the weight given by medical professional to anatomy via anatomy slider 1030, to reduce SRS to optimal set (OS)

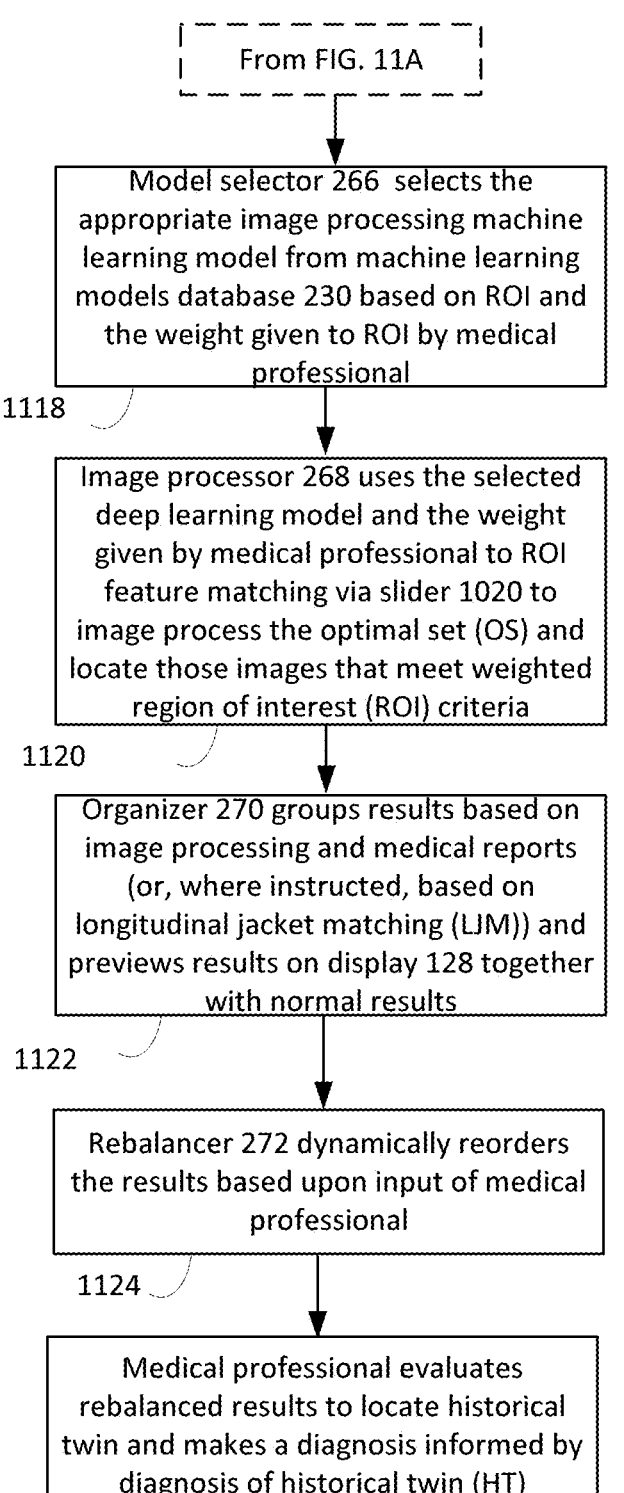

From FIG. 11A

Model selector 266 selects the appropriate image processing machine learning model from machine learning models database 230 based on ROI and the weight given to ROI by medical professional

1118

Image processor 268 uses the selected deep learning model and the weight given by medical professional to ROI feature matching via slider 1020 to image process the optimal set (OS) and locate those images that meet weighted region of interest (ROI) criteria

1120

Organizer 270 groups results based on image processing and medical reports (or, where instructed, based on longitudinal jacket matching (LJM)) and previews results on display 128 together with normal results

1122

Rebalancer 272 dynamically reorders the results based upon input of medical professional

1124

Medical professional evaluates rebalanced results to locate historical twin and makes a diagnosis informed by diagnosis of historical twin (HT)

1126

Region of interest (ROI) feature matching (cont'd from FIG. 11A)

FIG. 11B

1532

STRUCTURE 1502

MEMORY 1510

ANATOMICALLY ARRANGED ARCHIVE 1520

| BIN 1523A | BIN 1523N |
| BIN 1524A | BIN 1524N |
| BIN 1525A | BIN 1525N |
| BIN 1526A | BIN 1526N |
| BIN 1527A | BIN 1527N |

MACHINE LEARNING MODELS 1530

API 1512

PHYISICIAN-ASSISTING SOFTWARE 1540

ARCHIVER 1550

METADATA EXAMINER 1551

AI ARRANGER KEYS 1552

| XRAY 1553 | MRI 1554 |
| CT 1555 | PET 1556 |

UL-S 1557

IMAGE EVALUATOR 1558

HISTORICAL TWIN CIRCUMSCRIBER 1560

ANATOMY DETERMINER 1562

BENCHMARK APPLICATOR 1564

MODEL SELECTOR 1566

IMAGE PROCESSOR 1568

ORGANIZER 1570

REBALANCER 1572

API 1514

N/W INTERFACE 1508 ←→ PROCESSOR 1506

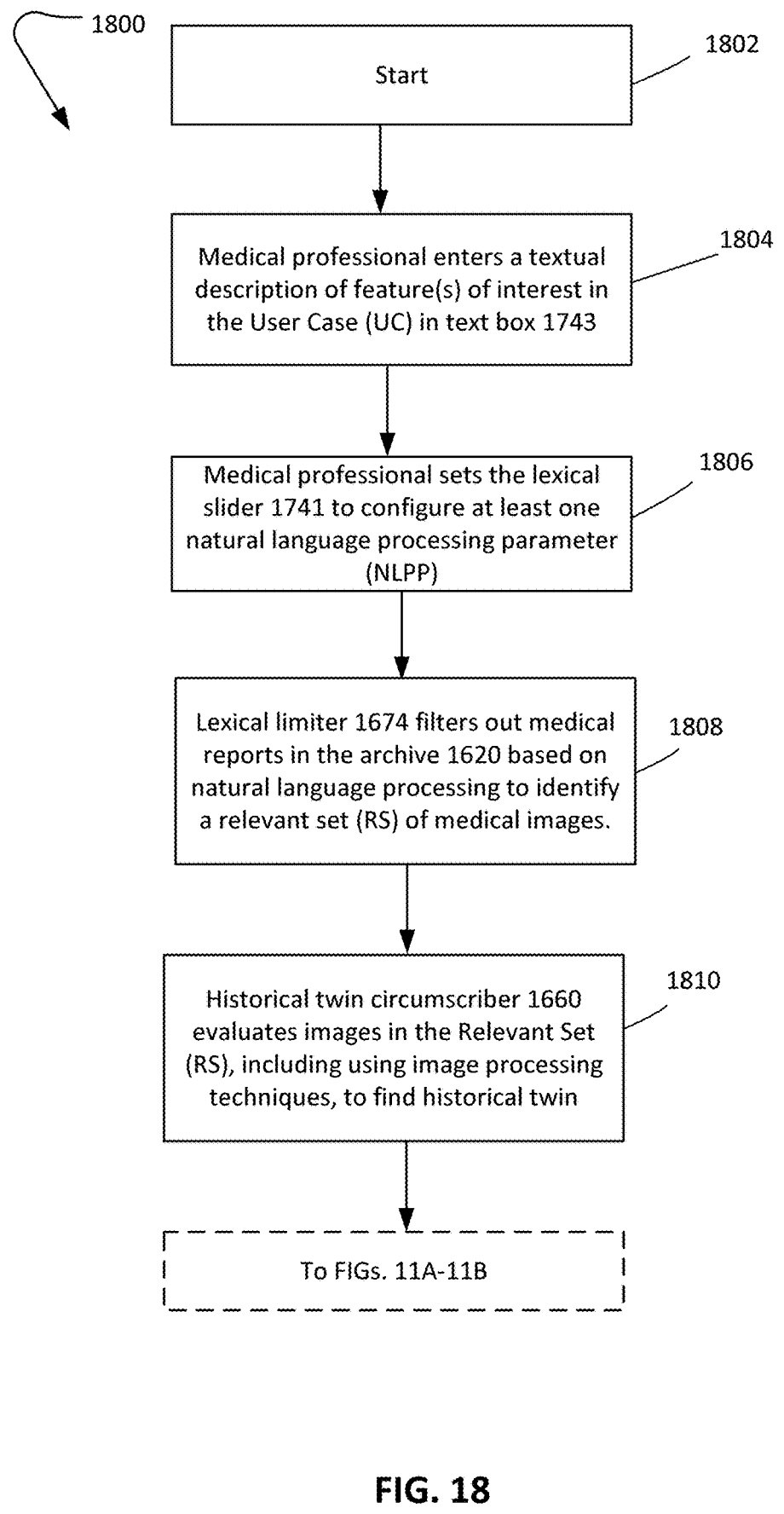

Start

1804

Medical professional enters a textual description of feature(s) of interest in the User Case (UC) in text box 1743

1806

Medical professional sets the lexical slider 1741 to configure at least one natural language processing parameter (NLPP)

1808

Lexical limiter 1674 filters out medical reports in the archive 1620 based on natural language processing to identify a relevant set (RS) of medical images.

1810

Historical twin circumscriber 1660 evaluates images in the Relevant Set (RS), including using image processing techniques, to find historical twin To FIGs. 11A-11B

FIG. 18

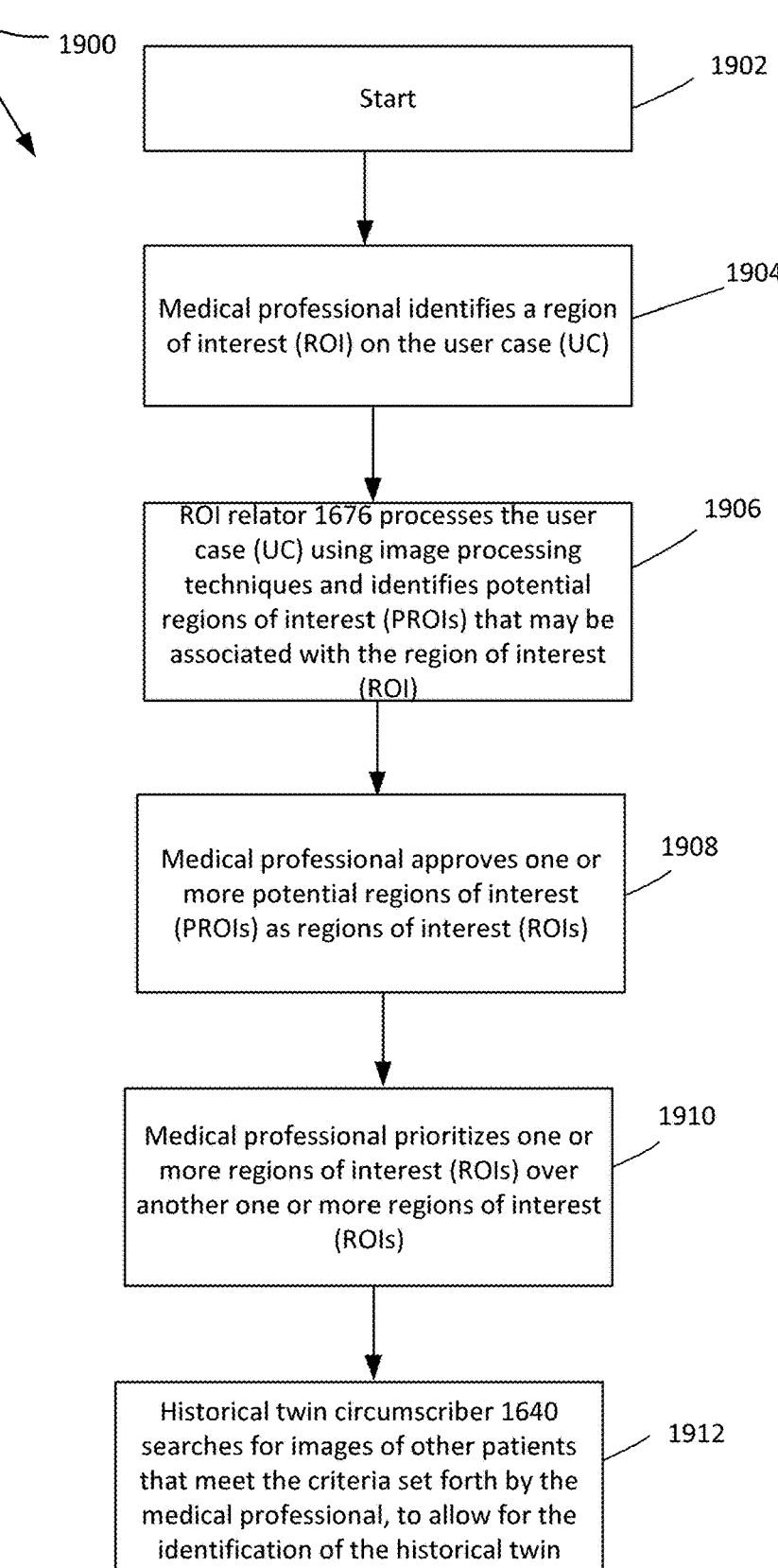

1900

1902 — Start

1904 — Medical professional identifies a region of interest (ROI) on the user case (UC)

1906 — ROI relator 1676 processes the user case (UC) using image processing techniques and identifies potential regions of interest (PROIs) that may be associated with the region of interest (ROI)

1908 — Medical professional approves one or more potential regions of interest (PROIs) as regions of interest (ROIs)

1910 — Medical professional prioritizes one or more regions of interest (ROIs) over another one or more regions of interest (ROIs)

1912 — Historical twin circumscriber 1640 searches for images of other patients that meet the criteria set forth by the medical professional, to allow for the identification of the historical twin

FIG. 19

PHYSICIAN-GUIDED MACHINE LEARNING SYSTEM FOR ASSESSING MEDICAL IMAGES TO FACILITATE LOCATING OF A HISTORICAL TWIN

CROSS-REFERENCE TO RELATED APPLICATIONS

This application is a continuation-in-part of U.S. patent application Ser. No. 17/202,913, filed Mar. 16, 2021, which will issue as U.S. Pat. No. 11,205,520, the contents of which are incorporated herein by reference in their entireties.

FIELD OF THE DISCLOSURE

The disclosure relates generally to the field of systems and methods for processing medical images. More specifically, the disclosure relates to machine learning systems and methods for assisting a physician in finding medically relevant images and information based on physician-defined criteria.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere herein.

In an embodiment, a computer-implemented method of evaluating a user image of a patient to enable identification of a historical twin of the patient comprises processing a plurality of medical images to determine an anatomic characterization of each of the plurality of medical images. The method comprises organizing each of the plurality of medical images in an archive using the determined anatomic characterization and metadata. The method includes displaying the user image using a graphical user interface. The method comprises receiving from a medical professional, in connection with the user image and via the graphical user interface, each of: (i) a region of interest; (ii) a textual description associated with the region of interest; (iii) a natural language search parameter; (iv) selections for binary criteria; and (v) weights of weighable criteria, including a weight to be given to each of: (v)(a) an anatomical location of the region of interest; and (v)(b) features of the region of interest. The method comprises using a natural language search configured using the natural language search parameter to create a relevant set of medical images from the archive. The method comprises creating an optimal set of medical images from the relevant set of medical images by discarding medical images from the relevant set of medical images based on the selections for binary criteria and the weight of the anatomical location of the region of interest, and image processing medical images in the optimal set using the weight of the features of the region of interest to create medical image results. The relevant set comprises less than ten percent of the plurality of medical images in the archive.

In another embodiment, a computer-implemented method of evaluating a user image of a patient to enable identification of a historical twin of the patient comprises organizing a plurality of medical images in an archive and displaying the user image using a graphical user interface. The method includes receiving from a medical professional, in connection with the user image and via the graphical user interface, each of: (i) a plurality of regions of interest; (ii) a textual description associated with at least one of the plurality of regions of interest; (iii) selections for binary criteria; (iv) priority information for prioritizing at least one of the plurality of regions of interest; and (v) weights of weighable criteria, including a weight to be given to each of: (v)(a) an anatomical location of at least one of the plurality of regions of interest; and (v)(b) features of at least one of the plurality of regions of interest. The method comprises using a natural language search to create a relevant set of medical images from the archive and creating an optimal set of medical images from the relevant set of medical images by discarding medical images from the relevant set of medical images based on the selections for binary criteria and the weight of the anatomical location of at least one of the plurality of regions of interest. The method includes image processing medical images in the optimal set using the weight of the features of at least one of the regions of interest to create medical image results. The relevant set comprises less than ten percent of the plurality of medical images in the archive.

In yet another embodiment, a computer-implemented method of evaluating a user image of a patient to enable identification of a historical twin of the patient comprises organizing a plurality of medical images in an archive and displaying the user image using a graphical user interface. The method includes receiving from a medical professional, in connection with the user image and via the graphical user interface, each of: (i) a region of interest; (ii) a textual description; (iii) selections for binary criteria; and (iv) weights of weighable criteria, including a weight to be given to each of: (iv)(a) an anatomical location of the region of interest; and (iv)(b) features of the region of interest. The method comprises using a natural language search to create a relevant set of medical images from the archive and creating an optimal set of medical images from the relevant set of medical images by discarding medical images from the relevant set of medical images based at least on the selections for binary criteria. The method includes image processing medical images in the optimal set using the weight of the features of the region of interest to create medical image results. The relevant set comprises less than ten percent of the plurality of medical images in the archive.

BRIEF DESCRIPTION OF THE SEVERAL VIEWS OF THE DRAWINGS

Illustrative embodiments of the present disclosure are described in detail below with reference to the attached drawing figures and wherein:

FIG. 2 schematically shows an example physician-guided machine learning system, in an embodiment;

FIG. 7 shows a flowchart illustrating a method of using an archiver of the physician-guided machine learning system of FIG. 2 for tagging and storing a medical image using metadata and hierarchical anatomy;

FIGS. 11A-11B show a flowchart illustrating a method of using the physician-guided machine learning system of FIG. 2 to assess medical images to assist in the identification of a historical twin;

FIG. 15 schematically shows a physician-guided machine learning system, according to another embodiment.

FIG. 18 shows a flowchart illustrating a method of using a lexical limiter of the physician-guided machine learning system of FIG. 16.

FIG. 19 shows a flowchart illustrating a method of using an ROI relator and prioritizer of the physician-guided machine learning system of FIG. 16.

DETAILED DESCRIPTION

Figure 1:
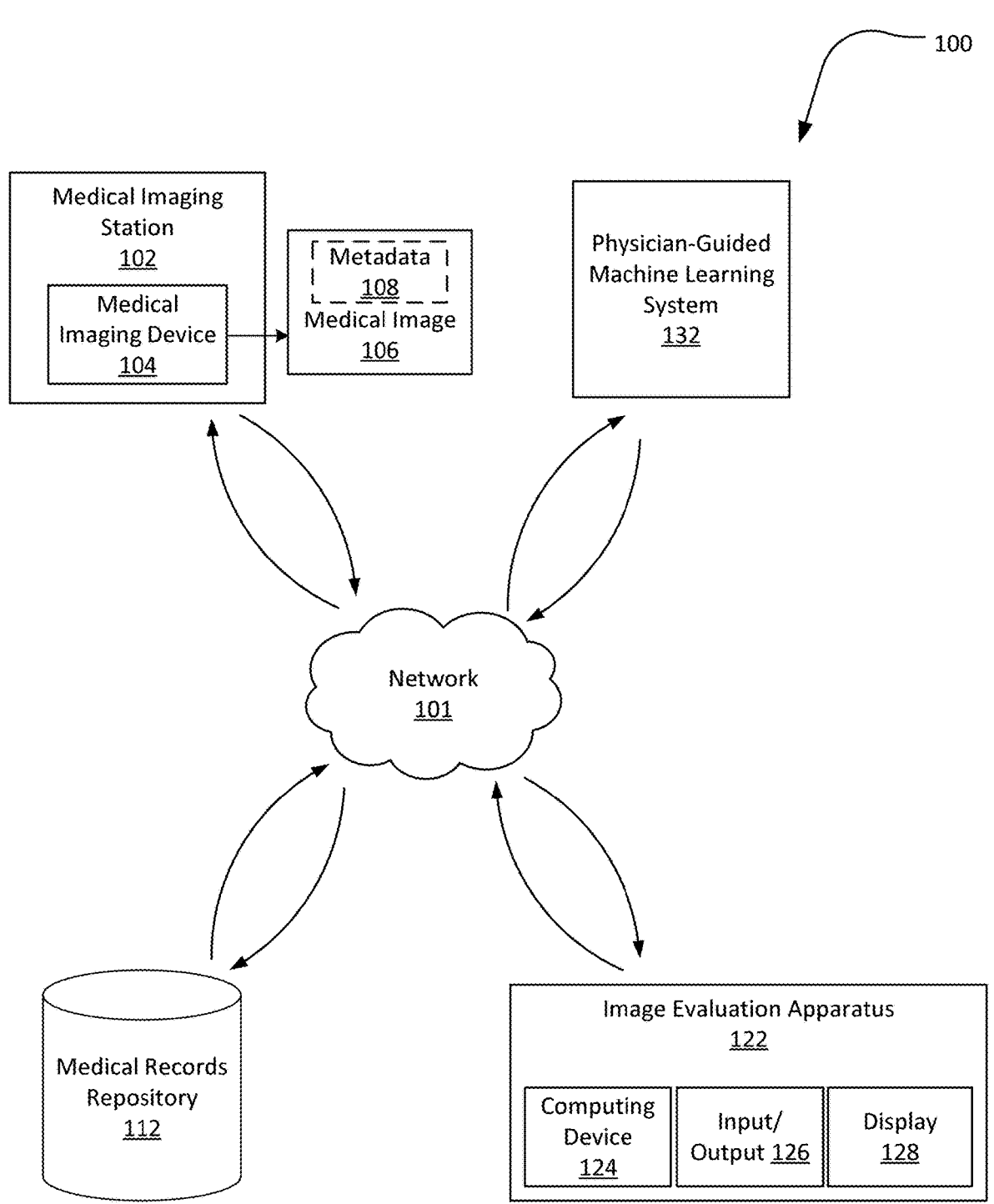
FIG. 1 schematically shows an example medical imaging environment, according to an embodiment.

Medical professionals employ medical imaging devices (e.g., magnetic resonance imaging (MRI) machines, computed tomography (CT) scanners, X-ray machines, ultrasound scanners, positron emission tomography (PET) scanners, et cetera) to generate images representative of the parts of the body to diagnose and treat diseases. The number of these medical images in existence is voluminous. According to some estimates, medical images account for about 90 percent of all medical data.

A solitary medical study may contain many images (e.g., a thousand images or more). Further, the number of images per exam has continued to increase over the years. A study conducted by the Mayo Clinic found that the average CT exam increased from 82 images in 1999 to 679 images in 2010, and the average MRI exam increased from 164 images in 1999 to 570 images in 2010. However, the number of cases a medical professional is required to evaluate on a daily basis remains largely unchanged. For example, an emergency room radiologist may be required to evaluate over 200 cases a day even today. These performance requirements limit the amount of time the medical professional may be able to devote to each image. In some cases, to meet workload demands, a medical professional (e.g., a radiologist) may be required to review an image every three to four seconds. Such workload demands may fatigue the medical professional reviewing the medical images and impact interpretation accuracy.

Efforts have been made in the prior art to employ artificial intelligence to reduce the workload of the medical professionals reviewing the images. The prior art solutions are focused on automatically making a particular diagnosis. Specifically, machine learning algorithms have been developed for rapidly and automatically detecting the presence of a predetermined feature of interest in a medical image using image recognition techniques, and if this feature of interest is found, making a diagnosis based on the presence of this feature. An example of a prior art machine learning medical image evaluation system is a system that is trained using a training set having many thousands of images to determine the presence of hemorrhage in brain MRI scans. Once trained, the prior art system may be able to rapidly and automatically evaluate a new brain MRI to determine the presence of hemorrhage, and if hemorrhage is identified, make a hemorrhage diagnosis. Another example of a prior art machine learning medical image evaluation system is a system that is trained to recognize pulmonary embolism in chest CT exams. Once trained, this prior art machine learning system may then rapidly and automatically run image process algorithms to evaluate a chest CT to determine the presence of pulmonary embolism, and if pulmonary embolism is identified, make a pulmonary embolism diagnosis.

The requirement of having manageable training sets to train the machine learning systems, coupled with the limitations of computer processing power and speed, severely limits the practical applicability of these prior art diagnosis-focused machine learning solutions. For example, the prior art system for evaluating brain MRI scans discussed above may excel at automating diagnosis of hemorrhage in brain MRIs, but may not be able to diagnose much else on a brain MRI. In practice, a medical professional may be interested in many different areas of a brain MRI for many different reasons (e.g., a brain MRI may exhibit a brain lesion in one area, malformations in other area(s), inflammation in the ventricles, et cetera), but a machine learning system that identifies only hemorrhage may be incapable of evaluating or even identifying these abnormalities. Further, it may not be feasible to train this prior art system to identify and/or diagnose every possible abnormality in a brain MRI, as such may take an unmanageable number of training sets. Even if a machine learning system could be trained to identify and diagnose every possible abnormality in a brain MRI, such a system may nevertheless be practically unusable-because of current limitations on processing power, it may take an exorbitant amount of time for this machine learning system to act on the expansive training sets, and consequently, this system may not be able to generate results in a meaningful amount of time. To obtain timely results with at least a modicum of accuracy, the diagnosis-focused machine learning systems of the prior art are trained to identify and diagnose only a small subset of medical conditions, but such also limits the practical applicability of these systems.

The present disclosure relates to machine learning systems and methods to assist a medical professional in evaluating medical (e.g., radiological) images. The disclosed machine learning systems and methods are not configured to make any diagnosis. Rather, they are configured to provide the medical professional with information, filtered by benchmarks set by the medical professional in line with the requirements of the particular case, to facilitate the finding of a historical twin and ultimately assist the medical professional in making a diagnosis. The term "medical professional," as used herein, means an imaging expert or other person that can take and/or examine a medical image, such as a radiologist or other physician, a medical resident or student, an imaging technician, a public health official, a patient, et cetera.

In more detail, a user interface may be provided to allow a medical professional reviewing an image of the patient at issue (also referred to as the "user image," or the "user case") to select certain searching benchmarks (B). The terms "user case" (or "user image" or "patient at issue" used interchangeably herein) may refer to a solitary patient image under consideration or a contiguous set of images which contain the feature of interest. Focus is directed to FIG. 8, which shows an example of the benchmarks B, in an embodiment. As can be seen, the benchmarks (B) may include: (I) a region of interest (ROI) in the user image identified by the medical professional; and (II) constraining criteria (CCR) set by the medical professional for that user image.

The region of interest (ROI) may be defined by the medical professional. Specifically, as discussed below, a user interface may be provided to allow the medical professional to identify a region of interest (ROI) in the user image being evaluated by the medical professional. The region of interest (ROI) identified by the medical professional may be any region of interest in the medical image which the medical professional considers germane to making or ruling out a diagnosis of the patient. For instance, the medical professional may identify a particular region of interest in a medical image because that region includes or potentially includes a clinically relevant abnormality (e.g., a lesion, cyst, inflammation, nodule, fracture, tear, et cetera).

The constraining criteria (CCR) may be set by the medical professional, as well. In an embodiment, the constraining criteria (CCR) may include each of: (1) binary criteria (BCR); and (2) weighted criteria (WCR).

Figure 8:
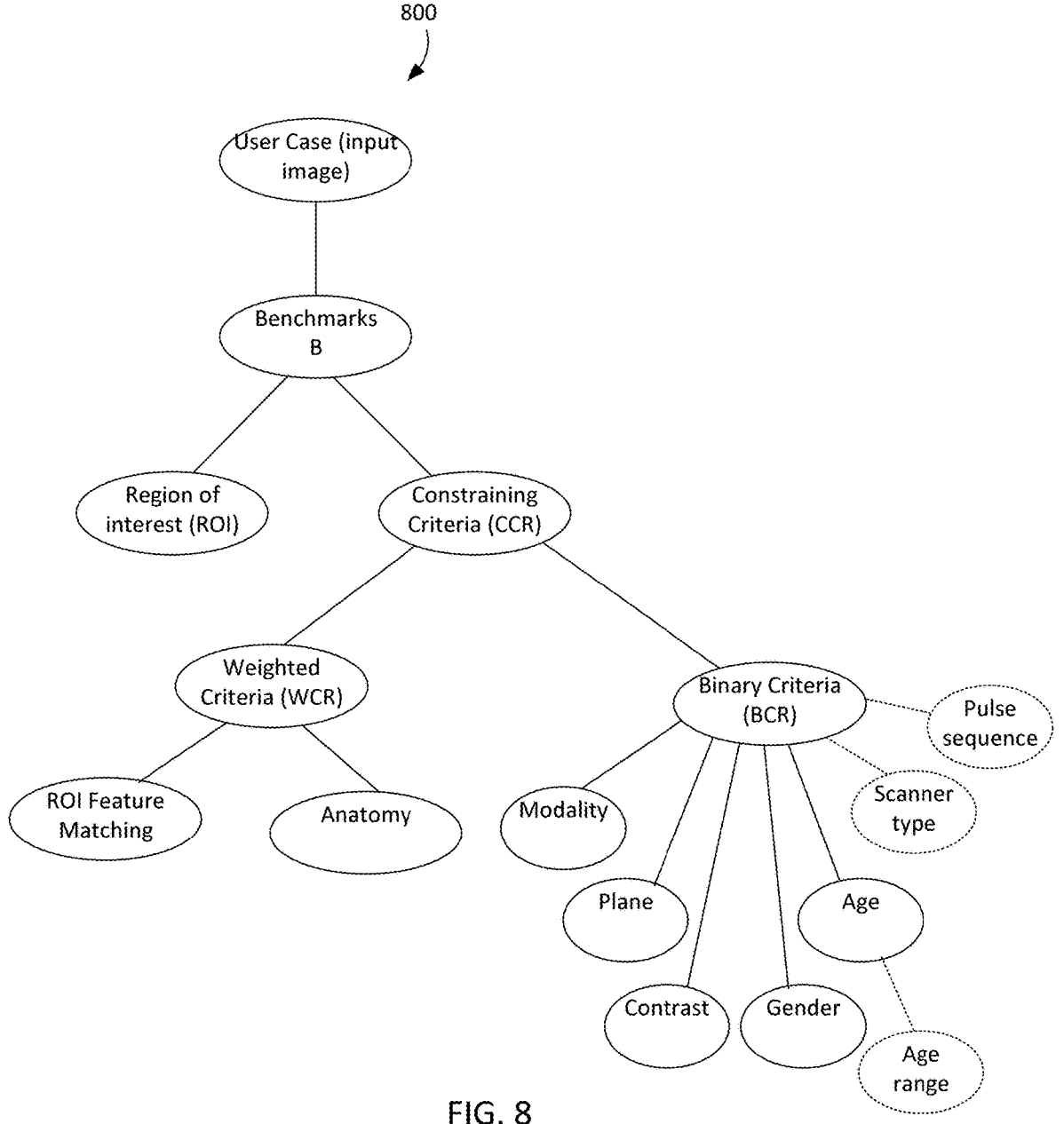
FIG. 8 schematically shows an example structure of physician-settable benchmarks for a user image, in an embodiment.

The binary criteria (BCR) may include one or more of: (i) modality; (ii) plane; (iii) contrast; (iv) gender; and (v) age. Other binary criteria (BCR) may be used as appropriate. For example, in embodiments, the binary criteria (BCR) may include scanner type, pulse sequence, or other appropriate binary criteria. As discussed herein, the binary criteria (BCR) available for selection by the medical professional may, in embodiments, depend on metadata associated with images. The binary criteria (BCR) may either be selected or disregarded by the physician, those being the two only options. In one embodiment, and as shown in FIG. 8, if the binary criteria (BCR) age is selected, the medical professional may further be able to specify an age range of interest.

The weighted criteria (WCR) may include: (i) anatomy; and (ii) region of interest feature matching (i.e., signal intensity matching within the region of interest). The weighted criteria (WCR), unlike the binary criteria (BCR), may be selectively weighted by the physician. For example, the physician may indicate the weight to be given to anatomy, and may separately indicate the weight to be given to the particular features of the previously identified region of interest (ROI), in the processing of the user image by the machine learning system disclosed herein. The weighted criteria (WCR) may also be referred to herein as "weighable criteria" (WCR), to indicate that the weights thereof may be selectively set by the medical professional.

The searching benchmarks (B)—i.e., the region of interest (ROI) and the constraining criteria (CCR) (e.g., each of the weighted criteria (WCR) and the binary criteria (BCR))—may be set by the medical professional based on the particular clinical question (regarding the patient at issue) the medical professional wants to ask. The disclosed system may then: (a) process images of other patients to locate images that meet the benchmarks B, including using image processing techniques, in an anatomically arranged archive that contains images and medical exam results of other patients; and (b) display results for evaluation by the medical professional. The machine learning techniques (e.g., the deep learning model(s)) employed by the system to evaluate the user case may depend on the particular searching benchmarks B set by the medical professional. The medical professional may then evaluate the results to identify a historical twin of the patient being examined. The term "historical twin," as used herein means a patient, other than the patient at issue, who has a medical image taken prior to the medical image of the patient at issue, and whose medical image is comparable to the medical image of the patient at issue such that the diagnosis of the historical twin may be used to inform the diagnosis of the patient at issue. For example, if the historical twin was diagnosed with a medical condition, the patient at issue may be diagnosed with the same (or a related) medical condition based on similarities between the medical image of the patient at issue and the medical image of the historical twin. In embodiments, the historical twin may be identified based solely on similarities between medical images of the patient at issue and the historical twin; in other embodiments, and as discussed herein, the historical twin may be identified based on an evaluation of the medical images of the patient at issue and the potential historical twin together with an evaluation of medical records of the patient at issue and the potential historical twin.

The images against which the search is run to locate the images that meet the benchmarks (B) may be organized in an archive according to relevant metadata and a novel, hierarchical anatomic standard (or schemas). As discussed herein, organizing the images to be searched by relevant metadata and the hierarchical anatomic standard may allow the machine learning system to discard a majority of the images in the archive out of hand, and thus, greatly limit the number of images in the archive that need to be evaluated by the system using image processing techniques. This filtering may exponentially reduce the computational load on the system. The system may then employ machine learning techniques (e.g., deep learning models) on the reduced dataset to find for the medical professional images and information that are responsive to the medical professional's query. The results may be arranged so as to allow the medical professional to rapidly and dynamically shift the focus to those results that the medical professional considers to be most relevant. In this way, and in part because of searching benchmarks B (including the weighted criteria (WCR) and the binary criteria (BCR) thereof selected by the medical professional specifically to formulate a tailored search for that user case), problems associated with the prior art diagnosis-focused systems may be avoided. A medical imaging evaluation (such as a radiology read being performed by a radiologist or a diagnostic evaluation by another qualified medical professional) may thus be greatly improved.

The machine learning analysis may be provided on behalf of any number of machine learning algorithms and trained models, including but not limited to deep learning models (also known as deep machine learning, or hierarchical models) that have been trained to perform image recognition tasks. Machine learning is used to refer to the various classes of artificial intelligence algorithms and algorithm-driven approaches that are capable of performing machine-driven (e.g., computer-aided) identification of trained structures, and deep learning is used to refer to a multiple-level operation of such machine learning algorithms using multiple levels of representation and abstraction. The artisan will understand that the role of the machine learning algorithms that are applied, used, and configured as described may be supplemented or substituted by any number of other algorithm-based approaches, including variations of artificial neural networks, learning-capable algorithms, trainable object classifications, and other artificial intelligence processing techniques.

FIG. 1 schematically illustrates an example medical imaging environment 100 for implementing the techniques described herein, according to an embodiment. The medical imaging environment 100 may allow for a medical image to be captured at one geographic location, stored at different geographical location, and reviewed by a medical professional at yet another geographical location with the aid of a machine learning system remote from the medical professional. In other embodiments, one or more of the various elements of the environment 100 as described herein may be co-located.

The environment 100 may include a medical imaging station 102, a medical records repository 112, an image evaluation apparatus 122, and a physician-guided machine learning system 132. While a solitary medical imaging station 102, medical records repository 112, image evaluation apparatus 122, and machine learning system 132 is shown in FIG. 1, the artisan will readily understand that the environment 100 may have any number of these elements. Each of the medical imaging station 102, the medical records repository 112, the image evaluation apparatus 122, and the physician-guided machine learning system 132, may be coupled to a network 101, which may be a wired network, a wireless network, or a combination thereof (e.g., the Internet, a local network, et cetera). The network 101 may be secured and/or encrypted.

The medical imaging station 102 may include a medical imaging device 104. The medical imaging device 104 may be one or more medical imaging devices, such as an MRI scanner, a CT scanner, an X-ray machine, an ultrasound scanner, a PET scanner, or another medical imaging modality. The medical imaging device 104 may be usable to generate a two-dimensional image 106 representative of the patient (e.g., representative of a limb, organ, or other body part of the patient). The medical imaging device 104 may also be usable to take a series of such two-dimensional images 106, which may in some cases be compiled into three-dimensional models.

The image 106 captured by device 104 may be consistent with the Digital Imaging and Communications in Medicine (DICOM) format, other industry-accepted standards, or proprietary standards, and may include metadata 108. The metadata 108 may be generated by the medical imaging device 104, or via other means (e.g., using the patient's EMR records, healthcare information system records, et cetera). When the images are formatted according to the DICOM standard, the metadata 108 may include a record number, a patient's name, gender, age, imaging modality, plane, a series identifier, information about techniques used to obtain the images, et cetera.

Each medical image 106 (together with the metadata 108) may be stored in the medical records repository 112, e.g., as a part of the medical report of the patient. The medical records repository 112 may be a computer, a server, a collection of servers, or other repository in which the image 106 and a large number of other medical images may be housed (e.g., as part of a medical exam of the patients which includes the physician's diagnosis reports). In the prior art, medical images are typically stored in a patient-centric manner (e.g., are organized by patient jacket so that a physician reviewing a medical image of a particular patient may review other medical images and reports of that patient which may have been taken at different points in time), and the medical images and data (e.g., physician's reports) may be so arranged in the medical records repository 112.

The image evaluation apparatus 122 may include one or more computing device 124, input/output device 126, and display 128. The computing device 124 may be any general purpose or special purpose computing device having a processor, memory, and software configured to enable the medical professional to examine medical images (e.g., the image 106) and provide a report thereon. The computing device 124 may be a mobile device. The input/output devices 126 may include a keyboard, mouse, joystick, voice recognition interface, gesture recognition interface, et cetera. The display 128 may be one or more displays (e.g., computer monitors, LCD screens, and such). In embodiments, the functionality of two or more of the computing device 124, input/output device 126, and display 128 may be combined into a single device (e.g., as a laptop, a touch screen device, et cetera). As discussed herein, image data from the medical records repository 112, and result data generated by the machine learning system 132, may be accessed by the medical professional via the image evaluation apparatus 122. The medical professional may be able to select the searching benchmarks B for a given image using the image evaluation apparatus 122, and once the results are generated by the machine learning system 132, may be able to optimize the results and record a diagnosis using the same image evaluation apparatus 122.

FIG. 1 further shows a physician-guided machine learning system 132 coupled to the network 101. This physician-guided machine learning system 132 is shown in additional detail in FIG. 2, to which focus is now directed.

Specifically, FIG. 2 shows a machine learning system 132 that assists a physician in making a diagnosis by providing to the physician clinically relevant images and information based on benchmarks (B) set by the physician. The machine learning system 132 is shown in FIG. 2 as an online structure 202. Online structure 202 may be implemented by one or more networked computer servers, and is shown with a processor 206 communicatively coupled to a network interface 208 and a memory 210. Processor 206 represents one or more digital processors. Network interface 208 may be implemented as one or both of a wired network interface and a wireless network interface, as is known in the art. In practice, network interface 208 may allow the machine learning system 132 to communicate with the medical records repository 112 and the and the image evaluation apparatus 122 over the network 101, e.g., via API 212 and 214, respectively.

Memory 210 represents one or more of volatile memory (e.g., RAM) and non-volatile memory (e.g., ROM, FLASH, magnetic media, optical media, et cetera). Although shown within structure 202, memory 210 may be, at least in part, implemented as network storage that is external to structure 202 and accessed via network interface 208.

Memory 210 may house an anatomically arranged archive 220, a database of machine learning models 230, and physician-assisting software 240. The archive 220, the database 230, and the software 240 may be stored within a transitory or non-transitory portion of the memory 210. As discussed herein, the physician-assisting software 240 includes machine readable instructions that are executed by processor 206 to perform the functionality of structure 202 as described herein.

The physician-assisting software 240 may include an archiver 250 and a historical twin circumscriber 260. The archiver 250 may include metadata examiner 251, artificial intelligence arranger keys 252, and an image evaluator 258. The archiver 250 may use the metadata examiner 251, the AI arranger keys 252, and the image evaluator 258 to tag and organize the images and data in the medical records reposi- tory 112 according to the metadata (e.g., metadata 108) and a novel hierarchical anatomical standard. The images in the repository 112, after they are tagged and organized by the archiver 250 according to metadata and anatomy, may be stored in the anatomically arranged archive 220 together with the data associated with these images. Alternately, the images may continue to be stored in the records repository 112, and the organizational tags (i.e., the metadata and hierarchical anatomical tags) may be stored in the archive 220. As discussed herein, in other embodiments, images in an archive usable by the machine learning systems disclosed herein may be tagged with anatomic tags that are not hierarchical.

As noted, the medical records repository 112 (FIG. 1) may be arranged in the conventional, prior art manner. Specifi- cally, as is known, the medical records repository 112 may be patient (or patient-jacket) centric. That is, the repository 112 may be arranged by patient. Once a medical professional accesses the data of a particular patient, e.g., by double clicking on the patient name, then all of the exams of that patient (e.g., a CT exam from 4 years ago, an MRI exam from 2 years ago, an X-ray exam from last week, et cetera) may be displayed. The physician may then access any of these exams to get a more complete picture of the patient's medical history. The medical records repository 112 as in the prior art ensures that the physician can quickly access all medically relevant data of the particular patient being evalu- ated by the physician.

The anatomically arranged archive 220, conversely, may not be patient-centric or jacket-focused. Rather, in the ana- tomically arranged archive 220, images may be arranged by metadata and anatomy. Thus, for example, multiple X-rays of the right foot of men in their twenties may be grouped together, even though these X-rays may belong to several different patients. In embodiments, the patient's name in the medical records repository 112 may not be stored in the archive 220 in view of HIPAA considerations; the archive 220 may include a record number of the patient, or a new record number may be generated to avoid any concerns related to protected health information (PHI). In embodi- ments, one or more medical reports associated with the image (e.g., a radiologist's or other physician's notes on the image, a general physician's diagnosis of the patient with whom the image is associated, et cetera) may likewise be stored in the archive 220 or in a different archive accessible by the system 132. A medical report may include a medical professional's description of the findings and diagnoses in a fixed set of images acquired at the same time, also referred to as an exam or study.

In more detail, the metadata examiner 251 may be con- figured to examine the metadata of each image in the repository 112 (e.g., metadata 108 of medical image 106) so that each image may be arranged according to this metadata. Further, the archiver 250 may use the AI arranger keys 252, together with the image evaluator 258, to process the images and determine the anatomy shown in each image, so as to allow each image to be further tagged by anatomy. Thus, each image may be tagged by both the metadata (by the metadata examiner 251) and the anatomy (by the image evaluator 258 employing the appropriate AI arranger keys 252). The tagged images may be grouped together (e.g., in electronic storage "bins") in the anatomically arranged archive 220 based on the metadata and determined anatomy to allow for efficient processing thereof.

In an example embodiment, and as shown in FIG. 2, the anatomically arranged archive 220 may have storage bins 223A-223N, 224A-224N, 225A-225N, 226A-226N, and 227A-227N. The storage bins 223A-223N may be config- ured to store X-rays, storage bins 224A-224N may be configured to store MRIs, storage bins 225A-225N may be configured to store CT scans, storage bins 226A-226N may be configured to store PETs, and storage bins 227A-227N may be configured to store ultrasounds. As discussed herein, the bins 223A-223N, 224A-224N, 225A-225N, 226A-226N, and 227A-227N may respectively correspond to AI arranger keys 253, 254, 255, 256, and 257.

The medical images in a particular bin may be grouped based on their metadata and anatomy. For example, X-ray storage bin 223A may include X-rays of the left feet of men in their twenties, X-ray bin 223B may include X-rays of the necks of women over fifty, X-ray bin 223C (not expressly shown) may include X-rays of the index finger of toddlers, and so on. X-ray storage bin 223N indicates that the ana- tomically arranged archive 220 may have any reasonable number of X-ray bins.

Similarly, MRI storage bin 224A may include brain MRIs of women in their twenties, MRI storage bin 224B may include chest MRIs of men over thirty, MRI storage bin 224C (not expressly shown) may include MRIs of hands of men in their seventies, and so on. Bin 224N indicates that the anatomically arranged archive 220 may have any reasonable number of MRI bins. In like manner, the storage bins 225A-225N, 226A-226N, and 227A-227N may be respec- tively configured to store CTs, PETs, and ultrasounds that are grouped together by the archiver 250. In an embodiment, all medical images showing a particular anatomy may be stored in the same bin, and metadata tags may be usable to drill down into a specific category of those images (e.g., in an embodiment, all X-rays of feet of both men and women of all ages may be stored in the same bin, and the gender metadata tag may be used to differentiate between images of men and women during a search).

Grouping the various medical images in this fashion may allow the software 240 and/or the medical professional to readily distinguish between normal and abnormal appear- ance. For example, where the MRIs of knees of several forty-year old men are grouped together, separating those MRIs that appear normal from ones that show an abnormal- ity may be readily effectuated.

In embodiments, the archiver 250, and specifically the arranger keys 252 thereof, may include separate keys for each of X-rays, MRIs, CTs, PETs, and ultrasounds. For example, the AI arranger keys 252 may include X-ray keys 253, MRI keys 254, CT keys 255, PET keys 256, and ultrasound keys 257. The image evaluator 258 may use these keys in processing the images (e.g., the image 106) to determine the anatomy shown therein. For example, the image evaluator 258 may use the X-ray keys 253 in pro- cessing the image in an X-ray to allow that X-ray to be anatomically tagged and stored in the anatomically arranged archive (e.g., in one of the X-ray bins 223A-223N). Simi- larly, the image evaluator 258 may use the MRI keys 254 to process the image in an MRI to allow the MRI image to be anatomically tagged and stored in one of the MRI bins 224A-224N. And so on.

Figure 3:
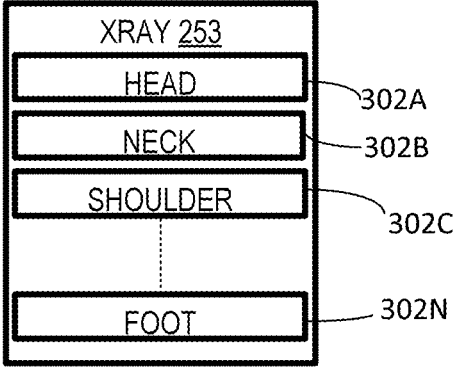
FIG. 3 schematically shows an artificial intelligence arranger key for medical images, X-rays in this example.

FIG. 3 shows the example X-ray key 253 in additional detail. The illustrated X-ray key has training sets 302A-302N. Training set 302A is shown to include information (e.g., image data) about head X-rays, training set 302B is shown to include information about neck X-rays, training set 302C is shown to include information about shoulder X-rays, and training set 302N is shown to include information about foot X-rays. In some embodiments, each training set may include subsets. For example, the head training set 302A may include a training set for X-rays of men's heads, a training set for X-rays of women's heads, a training set for X-rays of infants' heads, and so on. The X-ray key 253 may allow the image evaluator 258 to process any given X-ray and determine, e.g., by virtue of the training set 302A, whether a head (or another part of the body) is shown in the X-ray. The MRI keys 254 may likewise include a plurality of training sets (e.g., for brain MRIs, for foot MRIs, et cetera) and may allow the image evaluator 258 to process a given MRI image to determine the anatomy shown therein. Similarly, the CT keys 255 may allow the image evaluator to process CT images to determine the anatomy shown therein. And so on. The image, after it is anatomically tagged by the image evaluator 258 (and tagged according to metadata by the metadata examiner 251 as discussed herein), may be stored in the appropriate bin in the anatomically arranged archive 220.

As noted, the images (and associated data) in the medical records repository 112, after it is archived by the archiver 250 based on metadata and anatomy, may be stored in the anatomically arranged archive 220. The artisan understand that the metadata (e.g., metadata 108) may include many fields. Not all the metadata fields may be relevant to the workings of the physician-assisting software 240 or have an appreciable rate of return for locating a historical twin with relevant diagnostic possibilities. Further, if a separate bin (or search tag) was created for each metadata field, the number of bins in the anatomically arranged archive may become unmanageable. Therefore, the archiver 250, in using the metadata examiner 251 to evaluate the metadata of the images, may evaluate only those metadata fields that are of significance to the workings of the physician assisting software 240.

Figure 4:
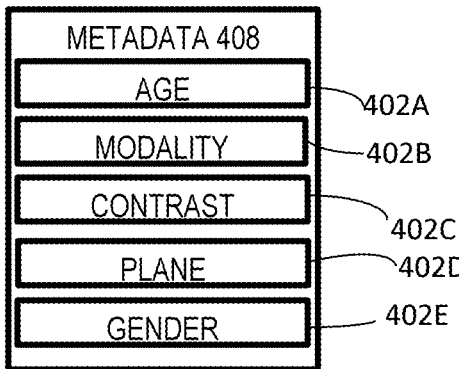
FIG. 4 schematically shows relevant metadata of a medical image, in an embodiment.

FIG. 4 shows metadata 408 which, in an example embodiment, is that subset of metadata 108 that is considered by the metadata examiner 251 in grouping the images for creating the archive 220. That is, in an embodiment, an image may be tagged by the metadata examiner 251 only with the metadata shown in FIG. 4. As can be seen, in the illustrated embodiment, the metadata considered by the metadata examiner in grouping the images based on metadata may include age 402A, modality 402B, contrast 402C, plane 402B, and gender 402E. The artisan will understand that listing is merely exemplary and that in embodiments, fewer or additional metadata fields may be considered. For example, because certain medical imaging devices (e.g., GE scanners) may render images having certain unique characteristics (e.g., an imaging artifact), in embodiments, the medical professional may be allowed to select the particular medical imaging device as a metadata constraint. Other potential metadata constraints may include pulse sequence, CPT codes, or other appropriate metadata.

As discussed herein, not all metadata fields may be useful to the software 240, and as such, in embodiments, the subset of metadata with which the images are tagged may include only metadata having an appreciable rate of return for locating a historical twin with relevant diagnostic possibilities. Anatomy, like metadata, may present a similar concern. Specifically, if the image evaluator 258 tagged images by anatomy that is very granular (e.g., at the vein level, nerve level, vessel level, et cetera), the number of bins needed to group the images may become unmanageable. On the other end of the spectrum, if the image evaluator 258 tagged images only by high-level anatomy (e.g., only by head, chest, leg, et cetera), each bin may end up having an unduly large number of images. In either case, the efficiency of the software 240 may be adversely affected.

Figure 5:
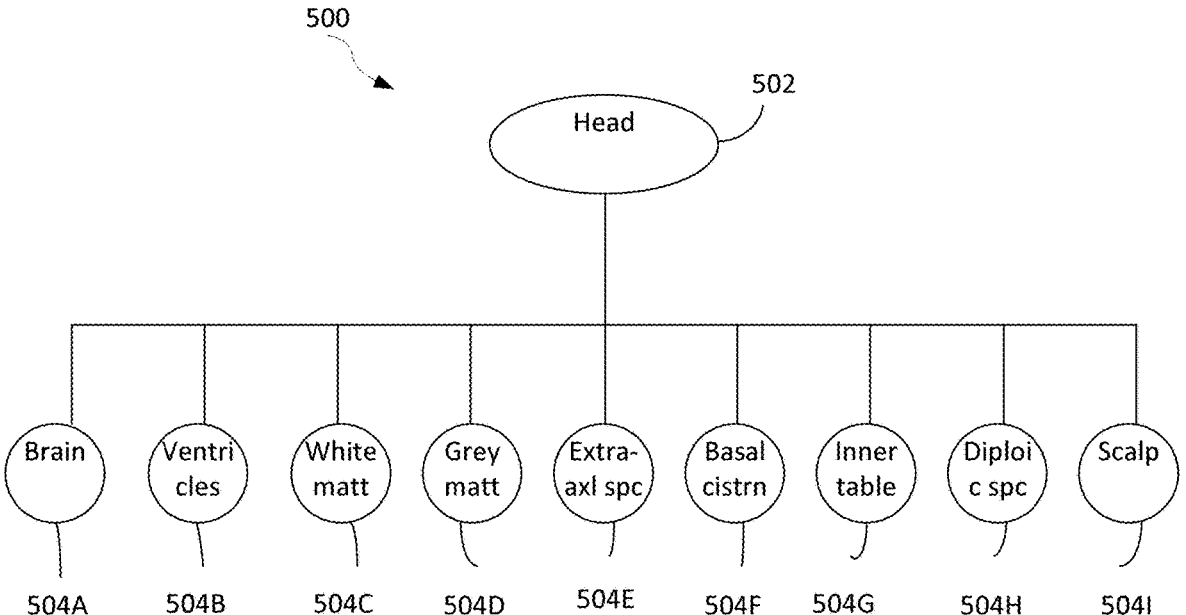
FIG. 5 shows an example hierarchical anatomical schema for organizing an MRI's of a patient's head.

To address these concerns, in an example embodiment, the image evaluator 258 may tag each image using a multi-level (e.g., a 2-level) anatomic hierarchy (i.e., one or more anatomic hierarchical schema). An example anatomic hierarchical schema is shown in FIG. 5 in the form of a tree structure. The tree structure of the anatomic hierarchy may have a primary root node and at least one secondary node (e.g., a parent node, a child node, a leaf node, et cetera).

In an example embodiment, each of the 206 bones in the human body and/or the 78 organs may form a root node. In this example, thus, there may be about 284 different possibilities for root nodes with which the image evaluator 258 may tag a particular image (e.g., an image may be tagged as showing the stomach (root node) and the antrum (leaf node), another image may be tagged as showing a facial bone (root node) together with orbits (leaf node), et cetera). The artisan will understand that these anatomic hierarchies may differ from one modality to the next (e.g., there may be 260 tree data structures for MRI scans and 200 tree data structures for X-rays). Having a hierarchical anatomic scheme that is unique to a given modality may allow the scheme to be used in educational settings to demonstrate, for example, the modality best suited for a particular anatomy, and the range of appearances based upon the selected anatomy and modality.

To illustrate, FIG. 5 shows one example hierarchical anatomical schema 500 that may be usable by the image evaluator 258 in processing an MRI of patient's head, so as to allow the processed image to be anatomically tagged and stored in the appropriate bin in the archive 220. As can be seen, the head MRI hierarchy may include a root node 502 (head) and secondary or leaf nodes. In this example classification, the leaf nodes are nodes 504A-504I (i.e., brain, ventricles, white matter, grey matter, extra-axial space, basal cistern, inner table, diploic space, and scalp, respectively). When the image evaluator 258 is processing an MRI in the repository 112 using the MRI keys 254, it may check whether the MRI is of a patient's head, and if so, tag the image with this root node and those secondary nodes that are determined to be present in the image. In some embodiments, the image evaluator 258 may include in the tag a probability that the particular anatomic structure is present. Depending on the weight the medical professional gives to a particular anatomy in the user image, the root node and/or the leaf node may be evaluated or disregarded by the historical twin circumscriber 260 (e.g., if the ROI is determined to have a 90% probability of containing a ventricle, and the medical professional places heavy emphasis on matching anatomy as discussed herein, then the historical twin circumscriber (or "recommendation generator") 260 may not evaluate an image in the repository 112 that has only a 10% probability of containing a ventricle). Of course, the complete set of hierarchical anatomical schemas may include the schema 500 for MRIs of patient's heads and multiple other schemas (e.g., a schema for stomach X-rays, a schema for foot MRIs, et cetera).

As noted, the archiver 250 may archive the image data in the repository 112 and arrange same in the anatomically arranged archive 220 such that the image data is arranged both by metadata and by anatomy. The workings of the archiver 250 will now be illustrated with an example.

Figure 6:
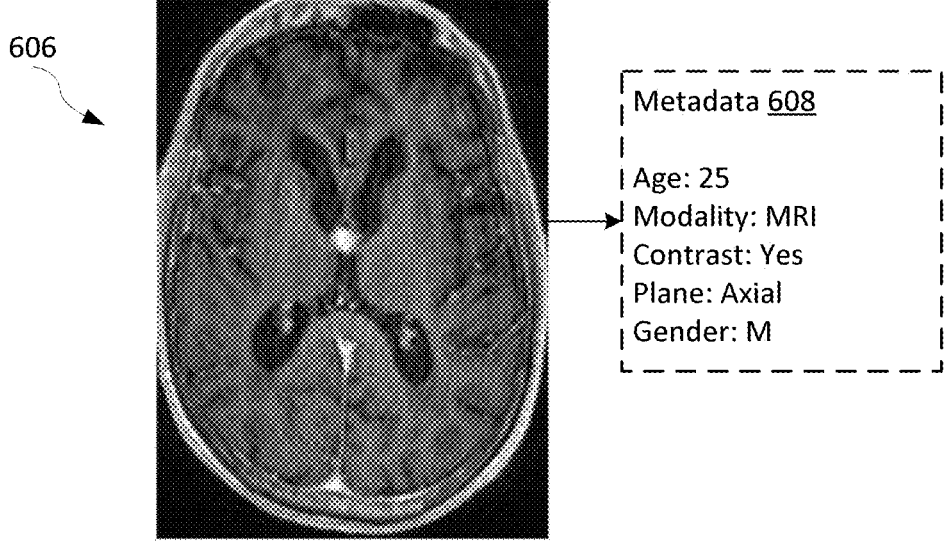
FIG. 6 shows an example MRI scan of a patient's head.

Consider, for instance, image 606 in FIG. 6, which may be an example of the image 106 (FIG. 1) located in the repository 112. This particular image is an MRI of the head of a patient. The scan includes metadata 608, which may be an example of the metadata 108. As can be seen, the metadata indicates in relevant part (see, e.g., metadata 408 in FIG. 4) that the image is a contrast-enhanced MRI scan of a man aged 25 in the axial plane. The image may also include additional metadata that is not considered by the metadata examiner 251. Assume that this image 606 resulted from an MRI scan conducted using the medical imaging device 104, and that it was thereafter stored in the medical records repository 112.

FIG. 7 shows a method 700 usable by the archiver 250 of the software 240 to evaluate an image in the repository 112, tag it with metadata and anatomy information, and store the tagged image and associated data (e.g., associated medical report) in the appropriate bin of the anatomically arranged archive 220. The method 700 may start at step 702. At step 704, the image 606 (or another image, e.g., the image 106) in the repository 112 may be fed to the archiver 250. At step 706, the metadata examiner 251 of the archiver 250 may evaluate the relevant metadata 608 and determine key definitions included therein. For instance, with respect to the image 606, the metadata examiner 251 may examine the metadata 608 and determine, in relevant part, that the image 606 is a contrast-enhanced MRI scan of a 25-year old male patient in the axial plane.

Next, at step 708, the archiver 250 may invoke the image evaluator 258 so that image processing techniques may be used to identify the anatomy shown in the image 606. At step 710, the image evaluator 258 may use the information gathered by the metadata examiner 251 to help determine the appropriate AI arranger keys 252 to use to image process the image 606. For instance, in this example, because the metadata 608 indicates the image is an MRI scan, the image evaluator 258 may employ the MRI keys 254 to process the image. More specifically, because the metadata 608 indicates the image is a contrast-enhanced MRI scan of a 25-year old male patient in the axial plane, the image evaluator 258 may employ the particular MRI key 254 configured for processing contrast-enhanced axial MRIs of men in their twenties (or if one is unavailable, the MRI key for processing contrast-enhanced axial MRIs of men of any age). In some cases, the metadata 608 may further indicate that the image is of the head of the patient; in such case, the image evaluator 258 may employ that MRI key 254 that is configured for processing contrast-enhanced axial MRIs of heads of male patients in their twenties. Alternately, the image evaluator 258 may employ all the contrast-enhanced axial-plane MRI keys 254 relating to men in their twenties (e.g., keys for recognizing a chest of such patients, keys for recognizing the shoulder of such patients, keys for recognizing the head of such patients, et cetera) and ultimately determine with high probability (e.g., 95% probability) that the MRI shows the head (root node 502) of the patient at step 712. The artisan will understand that the MRI key 254 relating to male patients in their twenties is merely exemplary, and that a different MRI key 254 may likewise be used (e.g., an MRI key for processing brain scans of men who are 18 and over).

Once the root node (head in this example) is ascertained at step 712, the image evaluator 258 may use the appropriate MRI keys 254 to determine the presence (or absence) of the leaf nodes in the tree structure (e.g., hierarchy 500 in FIG. 5), together with the probability that the leaf nodes are shown. For example, at step 714, and with respect to the image 606 shown in FIG. 6, the image evaluator 258 may ascertain that there is a: 95% probability that the scan contains the patient's brain (leaf node 50A), 87% probability that the scan contains ventricles (leaf node 504B), 90% probability that the scan contains white matter (leaf node 504C), 70% probability that the scan contains grey matter (leaf node 504D), 55% probability that the scan contains extra-axial space (leaf node 504E), 39% probability that the scan contains basal cisterns (leaf node 504F), 15% probability that the scan contains inner table (leaf node 504G), 12% probability that the scan contains diploic space (leaf node 504H), and 5% probability that the scan contains the patient's scalp (leaf node 504I).

At step 716, the image evaluator may tag the image 606 with the hierarchical anatomic tags HT (e.g., tags indicating image 600 has a 95% probability of showing a head, has a 95% probability of showing a brain, has a 87% probability of showing ventricles, and so on). Thus, at steps 712 through 716, the user image 606 may be organized by an appropriate hierarchical anatomical schema.

At step 717, the image 606 may be tagged with metadata tags MT (e.g., tags indicating image 600 is an MRI of a 25-year old male in the axial plane). At step 718, the image 606 may be stored with the metadata tags MT and the anatomic tags HT in the anatomically arranged archive 220, and specifically, in an appropriate bin thereof (e.g., bin 224E).

Figure 9:
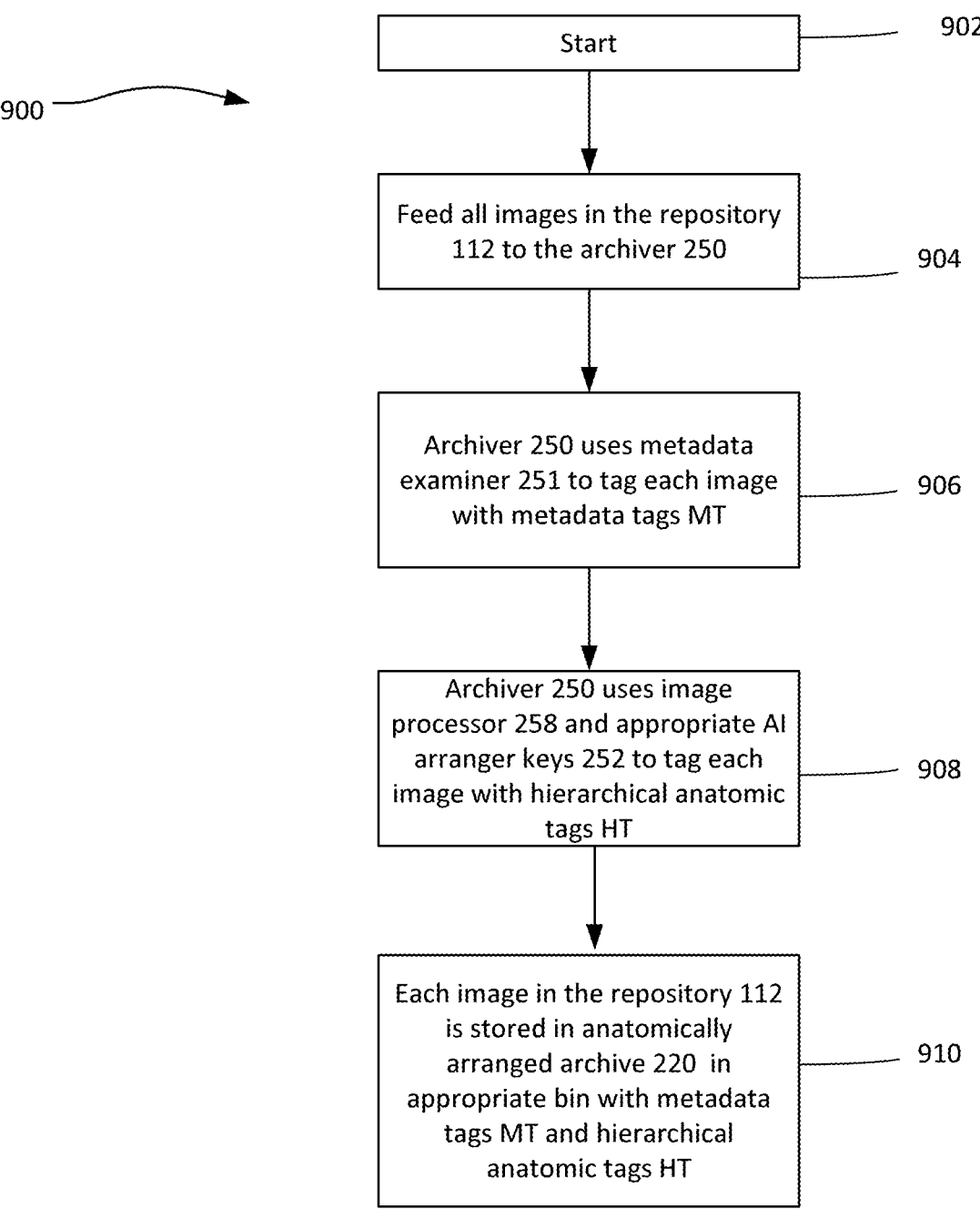
FIG. 9 shows a flowchart of using the archiver of the physician-guided machine learning system of FIG. 2 for tagging and storing a plurality of medical images using metadata and hierarchical anatomy.

FIG. 9 shows an example method 900 of generating the anatomically arranged archive 220. The method 900 may begin at step 902. At step 904, all images in the repository 112 may be fed to the archiver 250. These images may, e.g., be all or part of the images that have been taken using various medical imaging apparatuses in the environment 100 (e.g., in that facility or related facilities) over the course of time. At step 906, the archiver 250 may use the metadata examiner 251 to tag each image with the appropriate metadata tags MT. At step 908, the archiver 250 may employ the image evaluator 258, together with the AI arranger keys 252, to tag each image with the appropriate hierarchical anatomic tag HT. At step 910, each image in the repository 112 may be stored in anatomically arranged archive 220 in the appropriate bin with metadata tags MT and hierarchical anatomic tags HT (together with associated medical data, e.g., the physician's reports). The anatomically arranged archive 220 may, in essence, be a shadow archive of the repository 112, with the images in the repository 112 arranged as described herein. In some embodiments, the anatomically arranged archive 220 may only contain pointers to data (e.g., the images), and the image files may remain stored in the repository 112. The artisan will understand that the steps of method 900 need not be carried out in the order described; e.g., one image may be tagged with each of the metadata tags MT and hierarchical anatomy tags HT prior to the tagging of the next image.

Figure 10:
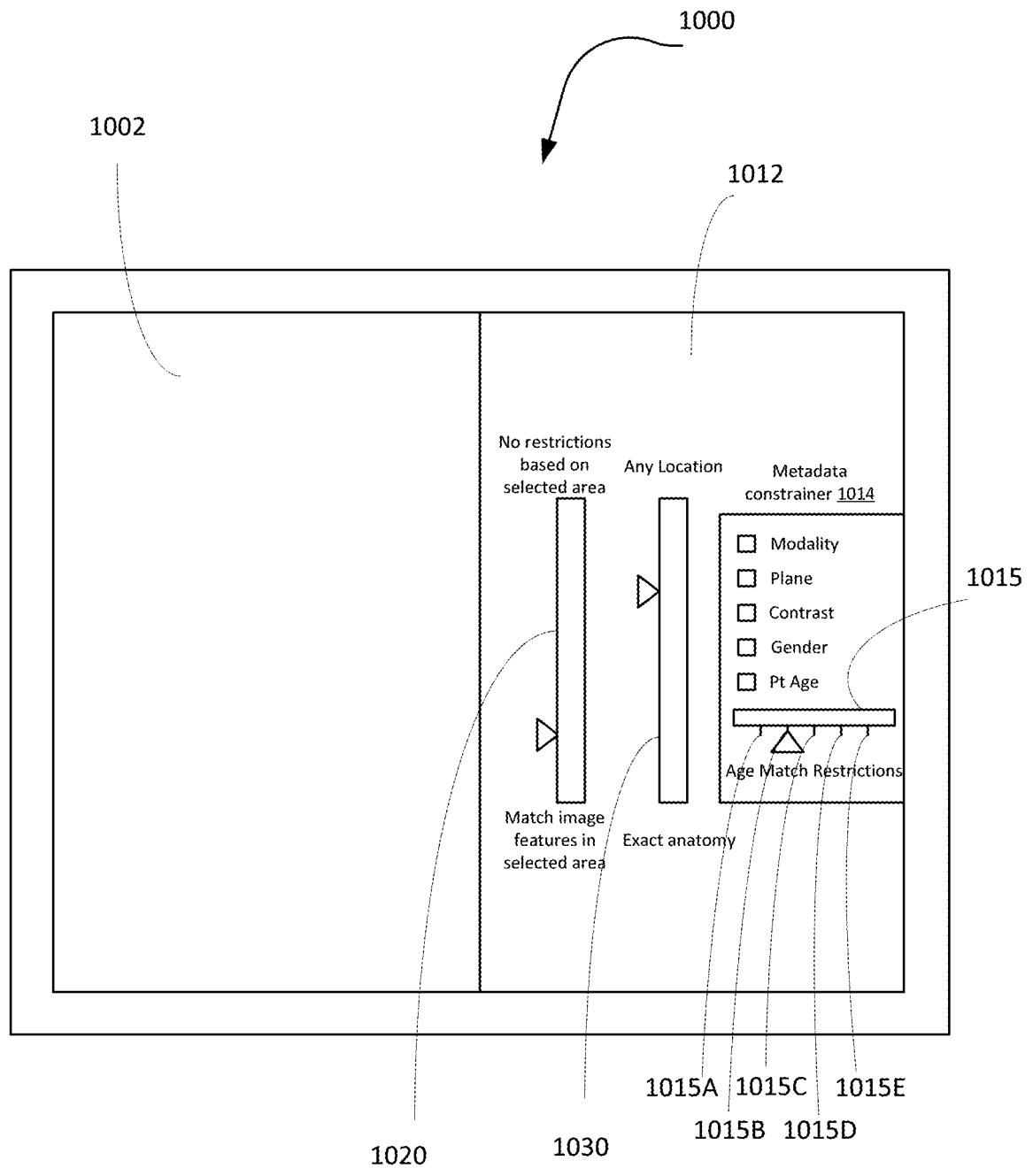
FIG. 10 schematically shows an example graphical user interface of the physician-guided machine learning system of FIG. 2, in an embodiment.

FIG. 10 shows a home screen of the graphical user interface 1000 usable by the medical professional in evaluating the user case to find a historical twin of the patient at issue. Using the input/output devices 126, the medical professional may interact with the user image by manipulating one or more user controls included in a graphical user interface 1000 presented at the display device 128. For example, the medical professional may view the user image (or a series of related images), and may specify one or more image adjustments, such as zooming, panning, rotating, changing contrast, changing color, changing view angle, changing view depth, changing rendering or reconstruction technique, and the like. Further, the medical professional viewing the user image may set the searching benchmarks B, i.e., identify the region of interest (ROI) (e.g., using a mouse or other means) and the constraining criteria (CC) (e.g., using the keyboard, mouse, or other means). Once the benchmarks B are set, the historical twin circumscriber 260 may search the anatomically arranged archive 220 and present results that include the historical twin of the patient with whom the user image is associated. The term circumscriber connotes that the historical twin circumscriber 260 does not necessarily identify the historical twin, but rather, using processing (including image processing and natural language) techniques, presents a confined grouping of results which includes or which is most likely to include the historical twin.

More specifically, the medical professional may use the home screen of the graphical user interface 1000 to select the benchmarks B for the search associated with the user image. The physician-assisting software 240 may then search the anatomically arranged archive 220 to find images (e.g., images of one or more other patients) that meet those benchmarks B. The medical professional may then evaluate the results to identify the image(s) that the medical professional considers to be most comparable to the user image. Once the physician finds the image that is most comparable to the user image, i.e., locates an image of the historical twin, the physician may review the medical history of the historical twin and inform the diagnosis of the user case with the diagnosis of the historical twin in the system. For instance, where a nodule in the MRI in the user case appears comparable to a nodule in the MRI of another patient/historical twin, the medical professional's diagnosis of the patient at issue may be informed by (e.g., be the same as) the diagnosis of the historical twin in the system. In effect, a medical professional may be able to review the side by side comparison of the patient at issue and the historical twin instead of having to rely on the medical professional's cognitive map, to increase the confidence in the diagnosis. In embodiments, the historical twin may be a solitary patient or a grouping of similarly situated patients.

The home screen of the graphical user interface 1000 may allow the medical professional to set benchmarks B for the search associated with the user case. In the illustrated embodiment, the home screen of the graphical user interface 1000 includes a region of interest (ROI) setting area 1002 and a constraining criteria (CCR) setting area 1012. As discussed herein, the medical professional may view a user case (e.g., an MRI scan, CT scan, et cetera) using the region of interest (ROI) setting area 1002 and identify the region of interest thereon.

The constraining criteria (CCR) setting area 1012 may have a metadata constrainer 1014, which may allow the medical professional to constrain the search by metadata. In an example embodiment, the metadata constrainer 1014 may allow the medical professional to selectively set the binary criteria (BCR) of the Benchmarks B for the search associated with the user image. For instance, in this example, the medical professional may use the metadata constrainer 1014 to select or disregard (e.g., by checking or unchecking) the modality, plane, contrast, and gender. As discussed herein, in embodiments, additional (or different) metadata constraints may be provided, e.g., scanner type, pulse sequence, et cetera.

The medical professional may likewise use the metadata constrainer to select or disregard age, and if age is selected, provide an age range. In the illustrated example, a tick mark age slider 1015 is provided having tick marks 1015A, 1015B, 1015C, 1015D, and 1015E. Tick marks 1015A, 1015B, 1015C, 1015D, and 1015E may respectively correspond to days, months, years, ten years, and twenty years, for example. If the age slider is set to one of the sliders (e.g., ten year slider 1015D), the physician assisting software 240 may evaluate in the anatomically arranged archive 220 only those images that are associated with patients that are up to ten years older or ten years younger than the patient at issue. The days tick mark 1015A may be particularly helpful when the user case is of an infant, as the imaging findings and applicable appropriate diagnoses of infants may change drastically in a matter of days.

The constraining criteria setting area 1012 may also include sliders for allowing the medical professional to selectively set the weighted criteria (WCR). In the illustrated example, the weighted criteria (WCR), i.e., the weight to be given to each of the ROI feature matching and the anatomy, may be set using a ROI slider 1020 and an anatomy slider 1030, respectively. Of course, other means may be employed to allow the medical professional to weigh the region of interest (ROI) feature matching and anatomy (e.g., the medical professional may be able to input numbers from a scale of 1 to ten to indicate the weighted criteria (WCR)).

The ROI slider 1020 may be usable to set a weight of the region of interest selected by the medical professional using the region of interest (ROI) setting area 1002. More specifically, if the ROI slider 1020 is set to its strictest setting (at the bottom of the slider in this example), the physician-assisting software 240 may include in its results only those images that include a generally identical region of interest. Conversely, the medical professional may selectively reduce the emphasis on (i.e., the weight given to) the region of interest (ROI) by moving the slider (towards the top in this example). For example, if the medical professional gives zero weight to the region of interest, the results may include images that are generally similar to the user image but which do not match with the user image on any specific feature.

The anatomy slider 1030 may allow the medical professional to attribute importance to the particular anatomy where the region of interest (ROI) is located. For example, if the anatomy slider 1030 is set to its strictest setting, the results may exclude those images that have a generally identical region of interest (ROI) but at a different location in the image. For instance, where the user case is a brain MRI, and the region of interest is a lesion in the center of the brain, setting of the anatomy slider 1030 to its strictest setting may cause the software 240 to exclude in its results those brain MRI scans that have a similar lesion located on the right side of the brain. Conversely, the weight given to the anatomy may be reduced by the medical professional by moving the slider 1030 (upwards in this example), in which case the MRIs of brains having a similar lesion in the right side of the brain may be made part of the results. Thus, the binary criteria (BCR) and the weighted criteria (WCR) may each be set by the medical professional to define search criteria (e.g., outline images in the archive 220 that may be filtered out because they are not responsive to the medical professional's query) but the weighted criteria may allow for the search constraints to be set more granularly.

Importantly, the benchmarks B are set by the medical professional based on the clinical question being asked. This is in part why the current AI solutions fail, because they are not able to dynamically alter the clinical question being asked based on the particular image (but instead, are relegated to answering the same question(s) for every image). The present disclosure, by allowing the benchmarks B to be set per image by the medical professional, assists in answering the particular clinical question with which the medical professional is concerned.

Consider, for example, that the user case may show a lesion in the spleen having a particular appearance. When searching for the historical twin, the medical professional may weigh the anatomy heavily (e.g., set the anatomy slider 1030 all the way down) because a spleen lesion is a specialized case and the appearance of a similar or even a generally identical lesion elsewhere in the body (e.g., in the legs, in the chest, et cetera) of other patients may be clinically irrelevant. Thus, when the user case shows a lesion in the spleen, the medical professional may employ a strict anatomy setting so that the results are generally limited to spleens of other patients. In embodiments, where the region of interest is in the center of the spleen, setting a restrictive anatomy setting may also exclude results that have a lesion (even a generally identical lesion) in the periphery of the spleen. Thus, anatomy may need to be heavily weighted where the user case shows a lesion in the spleen (i.e., anatomy may be heavily weighted where the image shows a lesion whose diagnosis is strongly informed by its location). Alternately, consider that the user case shows a chest nodule that can be a manifestation of systemic or other malignant diseases that can manifest in multiple locations in the lungs or even within bony structures. In that case, the medical professional may reduce the weight on anatomy (by moving the anatomy slider 1030 towards the top) because the medical professional may be less concerned with the particular anatomy in which the lesion manifests in the user case (e.g., in this case, an image of another patient's liver showing the same lesion features may be of more clinical interest to the medical professional in arriving at the diagnosis).

The weight given to the particular features of a region of interest (ROI) may likewise depend on the clinical question being asked. Region of interest feature matching may also be referred to herein as signal intensity matching, as in essence, region of interest feature matching may require the software 240 to match the pattern and relative intensities of pixels (e.g., black and white areas) of a given user image with corresponding areas in other images. Assume that the user case has the ROI on a contrast enhancing, spiculated lung lesion. The medical professional may understand this to be an unusual case, and therefore, the medical professional may choose a strict setting for the ROI slider 1020 (i.e., weigh the features of the region of interest (ROI) heavily) so that the results include only images having a similar or generally identical contrast enhancing lesion. Similarly, if the user case showed a lobulated soft tissue mass in the nasal cavity having flow voids, the medical professional may choose a strict setting for the ROI slider 1020 and the anatomy slider 1030 because the medical professional may want to review only those results which contain a similar or generally identical soft tissue mass specifically in the nasal cavity. Conversely, where the user case shows a tear in the Achilles, for example, the medical professional may deemphasize the region of interest (ROI) feature matching (and place more emphasis on the anatomy) because tears having a different appearance in the Achilles of other patients may be clinically informative.

The metadata constraints may likewise be set by the medical professional (using the metadata constrainer 1014) based on the particulars of the user case. Assume that the user case is an image of a kidney of an infant. The medical professional understands that the kidney of an infant may appear different from the kidney of an adult, or even a toddler, because an infant is often dehydrated, and that this dehydration can resolve itself over the course of a few days. Therefore, when searching for a historical twin, the medical professional may choose a narrow setting for age (e.g., by days) as the images of kidneys of toddlers or adults may not be clinically relevant. Alternately, if the user case included a kidney of a male adult, the medical professional may set the age match restrictions to plus/minus twenty years or disregard age completely.

Once the historical twin is located by the medical professional using the physician assisting software 240, the medical professional may make a diagnosis of the patient at issue informed by the diagnosis of the historical twin (which may have been made by a different physician). The medical professional evaluating the user case may therefore be able to quickly leverage the knowledge of many other physicians diagnosing comparable cases.

The workings of the archiver 250 are explained above. In brief, the artisan will understand from the disclosure herein that the physician-assisting software 240 may use the archiver 250 to rearrange images and data in the conventional patient-centric repository 112 by metadata and anatomy instead. Workings of the historical twin circumscriber 260 will now be described. In an example embodiment, the historical twin circumscriber 260 may comprise an anatomy determiner 262, a benchmark applicator 264, a model selector 266, an image processor 268, an organizer 270, and a rebalancer 272.

Focus is directed now to FIGS. 11A-11B, which show a flowchart illustrating a method 1100 of using the historical twin circumscriber 260 to assist in locating a historical twin of the patient at issue. The method 1100 may be implemented after the anatomically arranged archive 220 has been generated, using e.g., method 700 in FIG. 7 (for single image) and method 900 in FIG. 9 (application of method 700 to entire repository 112). The disclosure first outlines method 1100, and then illustrates the workings of method 1100 with an example. The artisan will understand that the steps of method 1100 (and the other methods described herein) need not be implemented in the order described or within a given timeframe.

Steps 1102 through 1108 may be used by the medical professional to set the benchmarks B for the search associated with the user image. Specifically, the method 1100 may start at step 1102, where the medical professional viewing a medical image of the patient at issue at the image evaluation apparatus 122 may use the graphical user interface 1000 to identify a region of interest (ROI) on the user case (UC). The medical professional may ensure that the region of interest (ROI) is suitably sized—i.e., defines the area of interest with specificity. If the region of interest (ROI) is unduly large (e.g., captures large areas about a lesion of interest), it may result in a significant number of unhelpful matches.

At step 1104, the medical professional may use the metadata constrainer 1014 of the graphical user interface 1000 to select binary criteria (BCR) for the user case (UC) evaluation. For example, the medical professional may indicate using the metadata constrainer 1014 that the images to be searched should be of the same modality as the user case (UC), and that the ages of the patients whose images are to be searched should be within 10 (or a different number) of years of the patient at issue.

At steps 1106 and 1108, the medical professional may select the weights of the weighted criteria (WCR). Specifically, at step 1106, the medical professional may use the ROI slider 1020 to indicate the weight to be given to the features of the region of interest (ROI) (i.e., the weight to be given to the signal intensity within the region of interest (ROI)). At step 1108, the medical professional may use the anatomy slider 1030 to indicate the weight to be given to the anatomy where the region of interest (ROI) is located. The artisan will understand that steps 1102, 1104, 1106, 1108 may be performed in any order (e.g., the medical professional may first select the weighted criteria (WCR) and then select the binary criteria (BCR)).

At step 1110, the benchmark applicator 264 may use the benchmarks B set by the medical professional to limit the set of images in the anatomically arranged archive 220 to be processed to a first reduced set (FRS). For example, if the medical professional selects a non-contrast MRI in the axial plane as benchmarks B (e.g., because the user case (UC) is a non-contrast MRI in the axial plane), the benchmark applicator 264 may eliminate from further consideration those images in the archive 220 that do not meet these benchmarks. Put another way, the benchmark applicator 264 may limit the first reduced set (FRS) to non-contrast MRIs in the axial plane (and exclude, for example: MRI scans in the sagittal and coronal planes, all X-rays, all CT scans, all PET scans, all ultrasounds, et cetera). Because of this filtering, the first reduced set (FRS) may include only a small percentage of the images (e.g., 1-10% of the images) in the anatomically arranged archive 220. Thus, the time required to image process the first reduced set (FRS) may be orders of magnitude less than the time it would have taken to image process the entire anatomically arranged archive 220. It will be understood that filtering out of the images on the basis of the benchmarks B will also result in filtering out any medical reports associated with these images.

At step 1112, the anatomy determiner 262 may call on the archiver 250, and specifically, the image evaluator 258 and AI arranger keys 252 thereof, to tag the user case (UC) with hierarchical anatomic tags (HT), and in so doing, may further limit the first reduced set (FRS) to a second reduced set (SRS). The anatomy identification of the user case (UC) may be effectuated in much the same way as was used to tag the images in the repository 112 with hierarchical anatomic tags HT for storage in the anatomically arranged archive 220. Use of the same methods for anatomically tagging the images in the repository 112 and anatomically tagging the user case (UC) may ensure consistency between the anatomically tagged images in the archive 220 and the user case (UC), and lead to reliable analysis. Thus, for example, if the anatomy determiner 262 determines at step 1110 that the image at issue (e.g., the MRI of a male patient in the axial plane, as determined by the binary criteria (BCR)) is an Achilles of the patient at issue, the first reduced set (FRS) may be reduced to the second reduced set (SRS) which only includes Achilles MRIs of male patients in the axial plane. Thus, each of the binary criteria (BCR) and the hierarchical anatomic tags (HT) may be used to reduce the number of medical images that will be image processed to find the features of the region of interest (ROI).

At step 1114, the image processor 268 may match the imaging technique of the user case (UC) and the second reduced set (SRS), so as to facilitate the dependable implementation of ROI feature matching algorithms. For example, where the user case (UC) is an X-ray, the attenuation of the user case (UC) and the X-rays in the second reduced set (SRS) may be normalized. Or, for instance, for other modalities, one or more of signal intensity, attenuation, reflected sound, et cetera, of the user case (UC) and the second reduced set (SRS) may be normalized or have field of view, technique, or other compensatory corrections applied, if needed, for an apples to apples comparison of the user case (UC) and the set of images being searched.

The machine learning models database 230 may house a plurality of machine learning models to match image features, and the model selector 266 may select the appropriate image processing model based on the particulars of the patient at issue. Specifically, once the second reduced set (SRS) of images in the anatomically arranged archive 220 has been identified, at step 1115, the model selector 266 may select the appropriate machine learning model from the machine learning models database 230 based on the generalized region of interest (ROI) and the weight placed on anatomy by the medical professional via the slider 1030. Assume, for example, that the user case (UC) is an X-ray of a woman's hand and the region of interest (ROI) is a possible hairline fracture in the index finger. Assume also that the anatomy is weighted heavily (via the slider 1020). In this case, the model selector 266 may select a deep learning model weighted towards hand x-ray feature matching, e.g., configured to find a major fracture, hairline fracture, nutrient foramen, variant trabeculae, et cetera, in index fingers.

At step 1116, the image processor 268 may employ the selected machine learning model to perform a perfunctory (i.e., high-level) feature match of the region of interest (ROI) based upon the relative location of the region of interest (ROI) in the user case (UC) and the weight given by the medical professional to anatomy via anatomy slider 1030, and in so doing, reduce the second reduced set (SRS) to optimal set (OS). Assume, for example, that the user case (UC) and the second reduced set (SRS) consists of brain MRIs of female patients in their twenties in the axial plane. Also assume that the medical professional identified the region of interest in the user case (UC) as a lesion in the center of the brain, and that the medical professional heavily weights the anatomy via the anatomy slider 1030. In this example, the image processor 224 may process the images in the second reduced set (SRS) and limit the optimal set (OS) to only those images that include a lesion (which at this point need not closely resemble the lesion in the ROI) in the center of the brain. Alternately, if the medical professional had placed medium weight on the anatomy, the image processor 268 may process the images in the second reduced set (SRS) and limit same to those images that include a lesion in the center of the brain or at a location proximate the center of the brain. As another example, if the medical professional had given very little weight to the anatomy via the anatomy slider 1030, the image processor 268 may have processed the second reduced set (SRS) and eliminated only those brain MRIs that did not include a lesion anywhere in the brain.

At step 1118, once the optimal set (OS) of images in the anatomically arranged archive 220 for image processing has been identified at step 1116, the model selector 266 may select the appropriate machine learning model from machine learning models database 230 based on the region of interest (ROI) and the weight placed on the region of interest (ROI) feature matching by the medical professional (via the ROI slider 1020). Assume, for example, that the user case (UC)

is an MRI of a toddler's lung and the ROI is a polygonal nodule. Assume also that the medical professional has weighted the ROI feature matching heavily. In this case, the model selector 266 may select a model configured for reliable feature matching (e.g., a model configured to locate polygonal nodules in images).

At step 1120, the image processor 268 may use the selected deep learning model and the weight given by medical professional to ROI feature matching via slider 1020 to image process the optimal set (OS) and locate those images that meet the weighted criteria specified for the ROI. These images (the first pass results) may thus be limited to images that meet all the benchmarks selected by the medical professional. The results may include only a small percentage (e.g., 0.001% to 1%) of the total images in the archive 220.

The organizer 270 may group the results as appropriate and preview the grouped results for the medical professional on the display 128 at step 1122. In embodiments, the results may be grouped by the organizer 270 based only on image processing outcomes (e.g., a user case (UC) brain MRI of a 50 year old patient showing a lesion in the center of the brain may be grouped together with a brain MRI of a 45 year old patient showing a generally identical lesion in the center of the brain; another group may include brain MRIs of post-operative patients with partial brain resection showing a generally identical lesion just to the left of the center of the brain; another group may include brain MRIs of patients showing a slightly differently shaped lesion but with similar pixel intensity maps in the center of the brain, et cetera).

In a currently preferred embodiment, the results may be grouped by the organizer 270 based on both image processing outcomes and medical reports (which have previously been reported by the same physician or a different physician) and results associated with the images in the results. In these embodiments, the organizer 270 may have natural language processing capability so as to allow for text in the medical reports of different patients to be compared. For example, an Achilles MRI of a patient reported as tendonitis may be grouped together with an Achilles MRI of another patient reported as tendonitis. In embodiments, the medical reports of each patient may be further evaluated to determine if an alternate diagnosis was discovered at surgery, in which case these two MRIs may be grouped separately. In an embodiment, the results displayed may also include normal results, for the medical professional's reference.

At step 1124, the medical professional may identify (e.g., by clicking on a grouping in the results) the group the medical professional considers more relevant to the user case (UC). Consider, for instance, that one group of results comprises X-rays showing a nondisplaced fracture and another group of results comprises X-rays showing a nutrient foramen. The medical professional may select one of these groups (e.g., the group showing nondisplaced fracture). Based on this input, the rebalancer 272 may dynamically reorder the set of results and display more X-rays showing the nondisplaced fracture variants and fewer or no X-rays showing similarly appearing but not relevant nutrient foramen matches. The rebalancer 272 may thus allow the medical professional to rapidly refocus the results to include those results that the medical professional considers to be most clinically relevant.

At step 1126, the medical professional may evaluate the rebalanced results to locate the historical twin(s) (HT), and may make a diagnosis for the user case (UC) informed by the diagnosis of historical twin. For example, the medical professional may diagnose the patient at issue in the same manner the historical twin was diagnosed. Or, for instance, the diagnosis of the historical twin may be used by the medical professional to inform the diagnosis of the patient at issue in another way (e.g., to rule out a diagnosis).

In this way, thus, the historical twin circumscriber 260 may take an archive 220 that may have many hundreds of thousands of images and circumscribe it (e.g., limit it to tens or hundreds of images) based on benchmarks B set by the medical professional so as to allow the physician evaluating the user case (UC) to leverage the decisions made by other physicians in clinically comparable cases.

Figure 12:
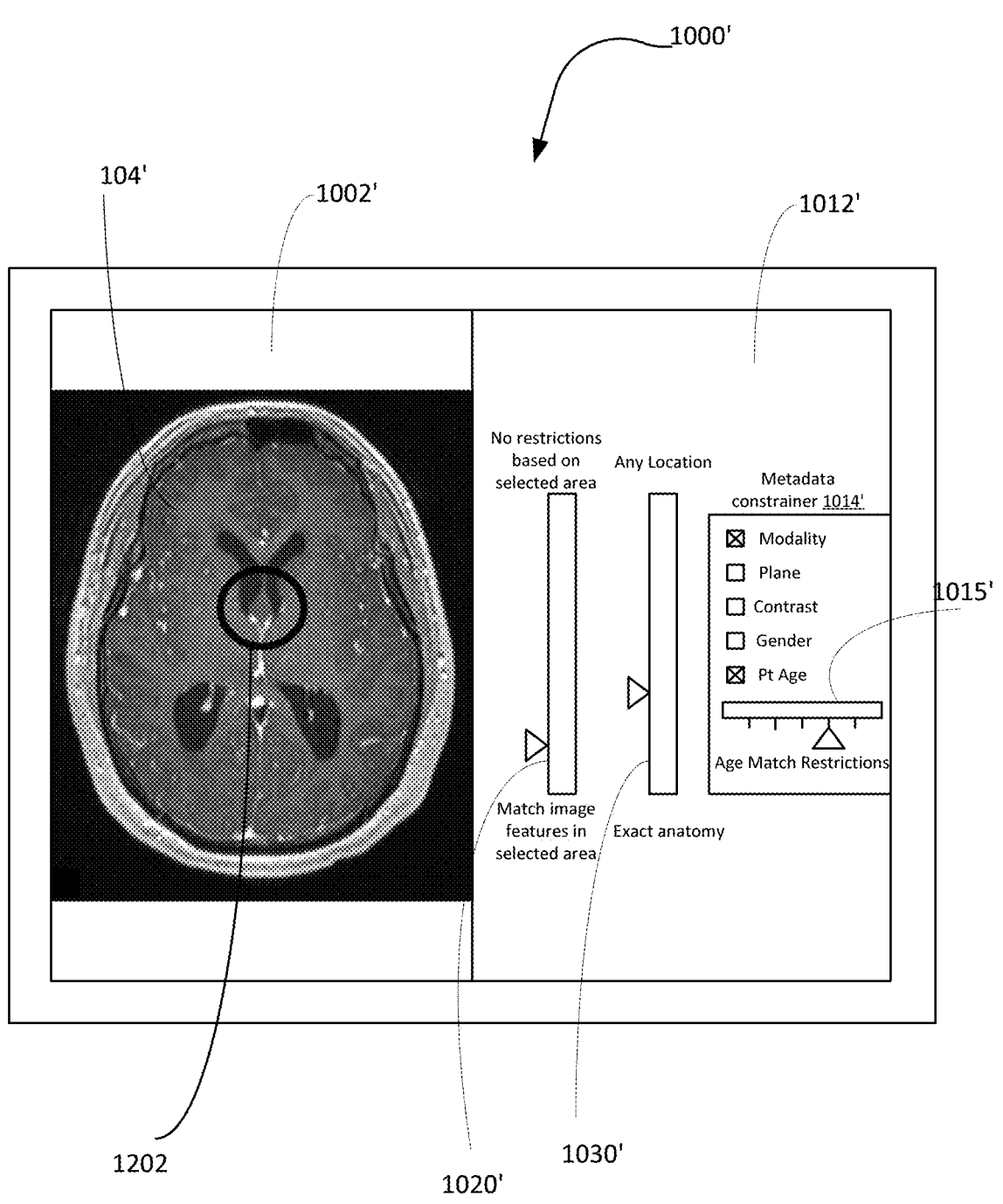
FIG. 12 shows the graphical user interface of FIG. 10 being used to identify the benchmarks for a medical image.

FIGS. 12, 13, and 14A-B show an example to illustrate workings of the method 1100. Specifically, FIG. 12 shows the interface 1000', which is an example of the interface 1000. ROI setting area 1002', constraining criteria (CCR) setting area 1012', ROI slider 1020', anatomy slider 1030', age scaled slider 1015' are examples of the corresponding components shown in FIG. 10. Corresponding numbers may likewise be used to show corresponding parts in this example, though with any noted deviations. As discussed, the method 1100 may be implemented after the anatomically arranged archive 220 has been generated.

As can be seen in FIG. 12, the medical professional is reviewing a brain MRI scan 104' (the user case (UC)). While not expressly evident from the figure, the MRI scan metadata indicates, among other things, that user case 104' is an MRI of a 40-year old patient.

At step 1102, the medical professional may identify the region of interest (ROI). For instance, the medical professional may identify the ROI 1202, which may in this example be a non-enhancing anterior midline nodule in the ventricle which is a colloid cyst.

At step 1104, the medical professional may select the Binary Criteria (BCR) using the metadata constrainer 1014'. In this example, the medical professional is shown to have selected modality (MRI in this case), plane (axial in this case), and patient age (40 years in this case; specifically, medical professional has set the age slider 1015' to plus/minus 10 years).

At steps 1106-1108, the medical professional may select the weighted criteria. Specifically, at step 1106, the medical professional may select the weight of the features of the region of interest 1202 via the ROI slider 1020', and at step 1108, the medical professional may select the weight of the regional anatomy of the region of interest 1202 via the slider 1030'. In this example, the medical professional is shown to have weighted the ROI features heavily relative to the anatomic location thereof.

Figure 13:
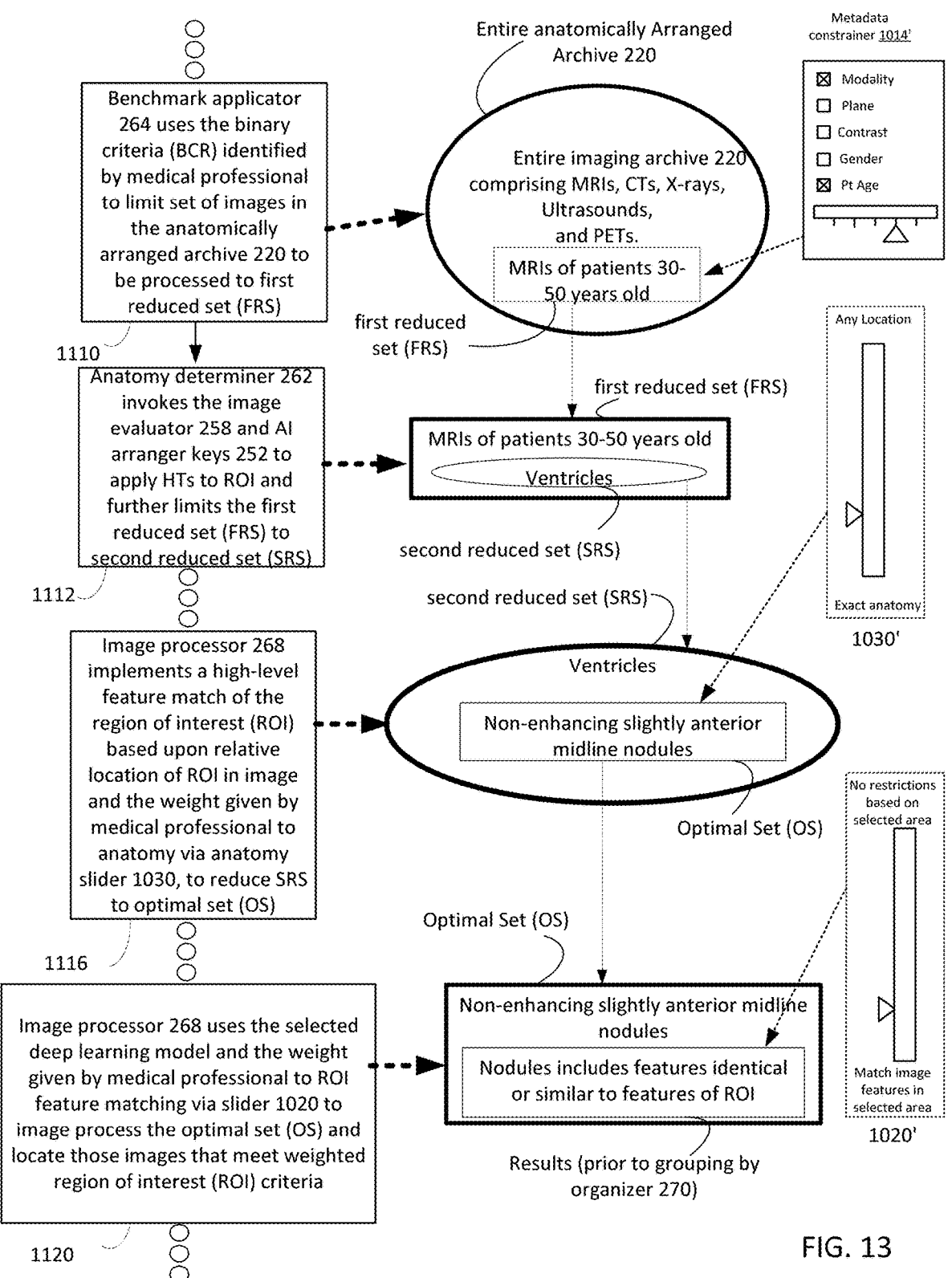
FIG. 13 schematically illustrates the way in which the number of images in an anatomically arranged archive to be image processed are reduced.

At step 1110, the benchmark applicator 264 may use the binary criteria (BCR) identified by medical professional to limit set of images in the anatomically arranged archive 220 to be processed to first reduced set (FRS). For instance, this example, the medical professional selected the modality and age (plus/minus ten years). The metadata indicates that the image is an MRI and that the patient's age is 40 years. Thus, based on the selected binary criteria (BCR), the benchmark applicator 264 may limit the set of images in the archive 220 to be processed to only those images that are MRIs and only those MRI's that are of patients who are between the ages of 30 years and 50 years. FIG. 13 schematically illustrates that the number of exams to be processed in the archive 220 has been reduced to the first reduced set (FRS).

At step 1112, anatomy determiner 262 may invoke the image evaluator 258 and AI arranger keys 252 to apply hierarchical anatomic tags HTs to user case (UC) 104' based on the region of interest (ROI), and in so doing, further limit the first reduced set (FRS) to second reduced set (SRS). For instance, in this example, the anatomy determiner may determine that the region of interest 1202 is the ventricle, and therefore, the first reduced set FRS (which contained MRIs of 30-50 year old patients) may be reduced only to MRI scans of 30-50 year old patients that include ventricles (leaf node 504B in FIG. 5). Reduction of the first reduced set (FRS) to the second reduced set (SRS) is schematically represented in FIG. 13.

At step 1114, image processor 268 may match the imaging technique of the user case (UC) 104' and the second reduced set (SRS). For example, the signal intensity of the user case 104' and the second reduced set may be normalized for a reliable comparison in subsequent steps. Alternately, or in addition, the image processor 268 may determine that the region of interest 1202 is non-enhancing, and therefore, may correspondingly limit the images in the second reduced set (SRS) to be processed.

At step 1115, the model selector 266 may select the appropriate machine learning model from the models database 230 based on the generalized features of the region of interest and the weight given by the medical professional to anatomy.

At step 1116, the image processor 268 may employ the selected machine learning model and implement a high-level feature match of the region of interest (ROI) 1202 based upon relative location of ROI in image and the weight given by medical professional to anatomy via anatomy slider 1030, and in this way, reduce the second reduced set (SRS) to optimal set (OS). In this example, at step 1116, the image processor 268 may determine that the ROI 1202 is a slightly anterior midline nodule. Therefore, considering that the medical professional has given substantial weight to anatomy via the anatomy slider 1030', the image processor 268 may limit the images to be further processed to include only those images that show a ventricle having a slightly anterior midline nodule, or a nodule proximate thereto. Reduction of the second reduced set (SRS) to the optimal set (OS) is schematically represented in FIG. 13.

At step 1118, the model selector 266 may select the appropriate machine learning model from machine learning models database 230 based on weight given to ROI by medical professional. For example, since the medical professional has heavily weighted the features of the ROI 1202 in this case, the model selector 266 may select a model configured to process MRI scans to identify the presence in the ventricle of a nodule having the particular appearance of the nodule in the user case.

At step 1120, the image processor 268 may use the selected deep learning model and the weight given by medical professional to ROI feature matching via slider 1020 to image process the optimal set (OS) and locate those images that meet weighted region of interest (ROI) criteria. In this case, the results of the processing of the image processor 268 may yield only those MRI scans that show non-enhancing slightly anterior midline nodules that have the specific features of the nodule in the region of interest 1202. This is schematically represented in FIG. 13.

At step 1122, the organizer 270 may group the results based on image processing and reports of medical professionals and display the results on display 128. The organizer 270 may also display normal brain scans for the medical professional's reference.

Figures 14A, 14B:
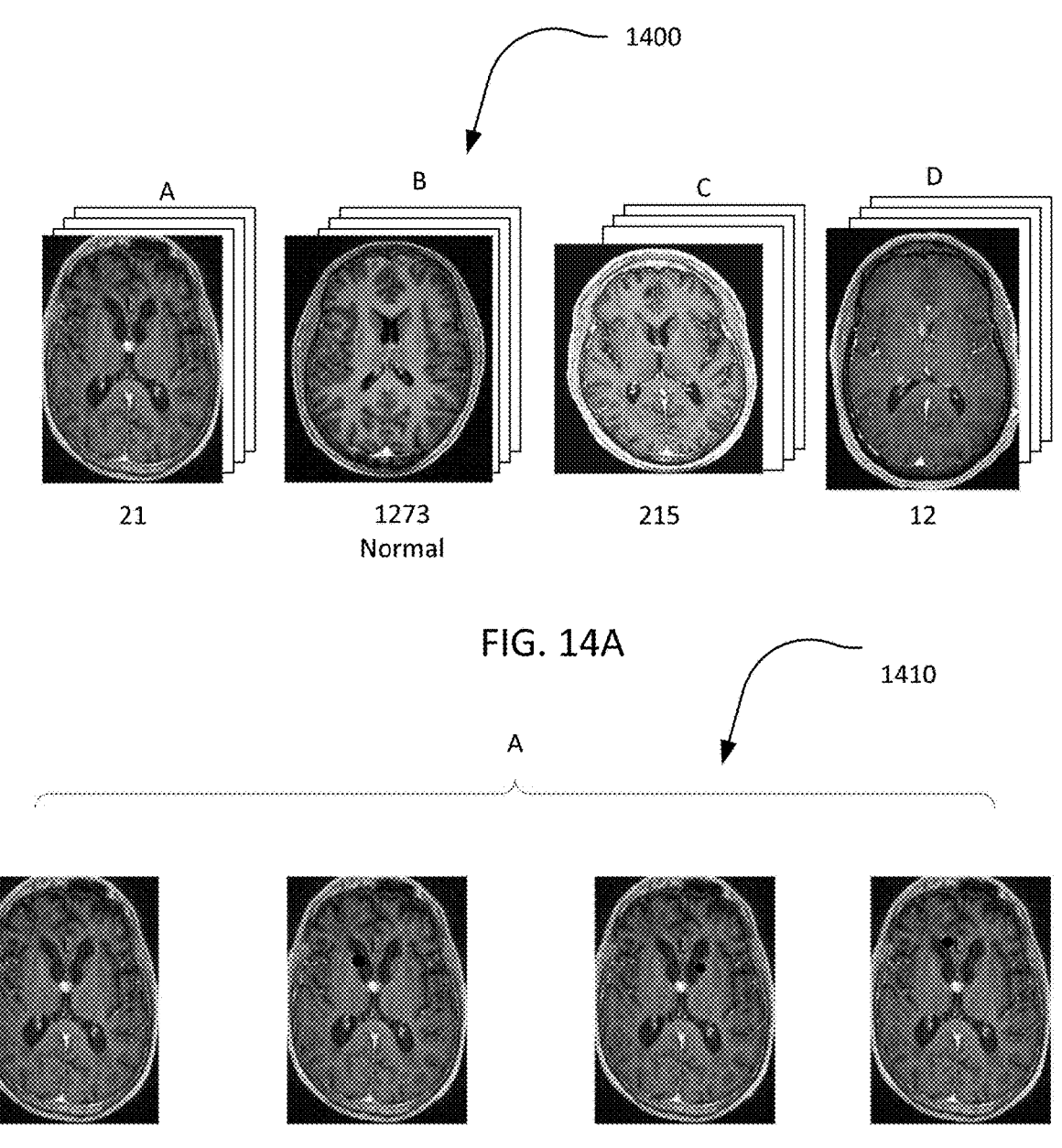
FIG. 14A shows an example results screen of the graphical user interface of FIG. 12 prior to rebalancing.
FIG. 14B shows an example results screen of the graphical user interface of FIG. 12 after the results have been rebalanced.

FIG. 14A shows an example results screen 1400 of the graphical user interface. In this example, the organizer 270 has grouped the results into four groups, group A, B, C, and D. Group A is shown to have 21 cases or potentially similar matches, group B is shown to have 1273 cases, group C is shown to have 215 cases, and group D is shown to have 12 cases. The groupings may be selected by the organizer 270 based on the results of the image processing (by the image processor 268) of these images, and optionally, also natural language processing of the medical reports associated therewith. Thus, in embodiments, the clustered results may convey the frequency of similar diagnoses based upon the number of potentially matching cases. For example, each of the 21 group A images may be grouped together because they all show an enhancing slightly anterior midline nodule and because the medical reports associated with each of these images indicates that the patient subsequently suffered from an aneurysm. Or, for instance, each of the 215 group C images may be grouped together because they all show a generally identical non-enhancing slightly anterior midline nodule.

As can be seen, group B is designated as normal, and may in embodiments be displayed for the medical professional's reference.

The medical professional may hover (e.g., using mouse or other input/output device 126) over any of the groups, and clinical information that is most likely to include the diagnosis may be displayed (i.e., hovering over an image in a group may cause that part of the physician's report to be displayed which most likely includes the diagnosis of the physician reviewing that particular image). If the medical professional moves the mouse over to the text, the entire medical result may be displayed. In this way, the medical professional may be able to quickly review the diagnoses of various images, and where clinically relevant, even the entire medical record associated therewith.

At step 1124, the rebalancer 272 may dynamically reorder the results based on input of medical professional. Consider, for example, that the medical professional selects group A because the images in group A are most relevant to the user case (UC). As shown in FIG. 14B, the rebalancer 272 may deprecate the results in groups B, C, and D, and display the results in a rebalanced results screen 1410 such that the images in group A are displayed more prominently. The medical professional may in embodiments be allowed to go back to the original results screen 1400 and rebalance the results in a different manner.

At step 1126, the medical professional may evaluate the rebalanced results to locate a historical twin(s). For example, the historical twin(s) may be the patient(s) associated with the image that is most comparable (i.e., clinically relevant) to the user case 104'. The medical professional may evaluate how the historical twin(s) was diagnosed, and if appropriate, diagnose the patient associated with the user case (UC) 104' in the same way (or otherwise diagnose the user case (UC) 104' such that the diagnosis is informed by the diagnosis of the historical twin). In this way, the medical professional may be able to leverage his knowledge (e.g., in identifying the region of interest and setting the benchmarks B) to ask the appropriate clinical question, and may further leverage the knowledge of other physicians who have answered that clinical question in other cases.

In some embodiments, at step 1122, if so instructed by the medical professional, the organizer 270 may "longitudinally match" the results prior to previewing the results. As noted, the organizer 270 may group the results based on image processing results and the medical reports associated therewith. Thus, for example, where the image being processed is an MRI of a potential historical twin, the organizer may consider the MRI and the medical report associated with that MRI (along with the MRI of the patient at issue). However, in embodiments, the organizer 270 may expand its search criteria where the medical professional instructs the organizer 270 to implement longitudinal matching. Specifically, where the longitudinal matching option is selected, the organizer 270 may compare the entire jacket of the patient at issue with the entire jacket of the potential historical twin(s), using, e.g., natural language processing techniques. For example, if the jacket of the patient at issue whose MRI is under review also includes a CT scan that indicates that he had to undergo surgery last year, the organizer 270 may attach additional importance to a potential historical twin whose jacket also indicates he had to undergo surgery in the last few years. Or, for instance, if the jacket of the patient at issue indicates the patient was once diagnosed with an aneurysm, the organizer 270 may attach additional importance to a potential historical twin whose jacket likewise includes a diagnosis for an aneurysm. In this way, software 240 may allow the medical professional to locate the historical twin based on not just the base image but also the entire medical timeline of events and data of the patient at issue and the historical twin candidates. The artisan will understand from the disclosure that the teachings hereof may be applicable to matching medical records of similarly situated patients based on user-provided criteria not primarily focused on imaging (e.g., comparisons based on medication lists, diagnoses, problem lists, et cetera).

While the disclosure above indicates that the medical professional selects the benchmarks B, in some embodiments, the benchmarks B may be auto-generated based on presets for certain image types and/or best practices (e.g., in cases where the medical professional does not wish to be overly prescriptive). For example, the machine learning system 132 may automatically limit the age range when the image in question is of a pediatric patient.

FIG. 15 shows a machine learning system 1532 that may assist a physician in making a diagnosis by providing to the physician clinically relevant images and information based on benchmarks B set by the physician, according to another embodiment. Aspects of the machine learning system 1532 in FIG. 15 may be identical or similar to those of the machine learning system 132 shown in FIG. 2, except as noted herein or would be apparent or inherent. Further, those skilled in the art will appreciate that the system 132 (and thus the system 1532) may be modified in various ways, such as through incorporating all or part of any of the various described embodiments, for example. In the interest of uniformity and brevity, corresponding reference numbers may be used to indicate corresponding parts. For example, API 1512 of system 1532 may be generally identical to API 212 of system 132, processor 1506 of system 1532 may be generally identical to processor 206 of system 132, the network interface 1508 of system 1532 may be generally identical to network interface 208 of system 132, and so on. Other components, e.g., AI arranger keys 1552, image evaluator 1558, anatomy determiner 1562, et cetera, of the system 1532 may generally correspond to the AI arranger keys 252, image evaluator 258, and anatomy determiner 262 of system 132, respectively, but as will become clear, may not be identical thereto.

A primary difference between the machine learning system 132 and the machine learning system 1532 may relate to the anatomically arranged archives 220 and 1520 thereof. Components of the machine learning system 1532 usable in creating the archive 1520, e.g., the AI arranger keys 1552, the machine learning models 1530, the anatomy determiner 1562, et cetera, may thus differ in relevant respects from the components of machine learning system 132 usable to create the archive 220, e.g., the AI arranger keys 252, the machine learning models 230, and the anatomy determiner 262.

Specifically, and as discussed above (see FIGS. 2, 5, 7, and 9), medical images stored in the anatomically arranged archive 220 of system 132 may be tagged with metadata tags MT and anatomic tags HT. As also described above, the anatomic tags HT associated with medical images in the archive 220 of system 132 may be hierarchical. For example, with respect to the machine learning system 132, when the image evaluator 258 processes an MRI in the repository 112 using the MRI keys 254, it may check whether the MRI is of a patient's head, and if so, tag the image with a root node (head, in this example) and those secondary nodes that are additionally determined to be present in the image (see FIG. 5). Conversely, images in the anatomically arranged archive 1520 of system 1532 may be tagged with metadata tags MT and anatomic tags AT that are "flat" or non-hierarchical. Each anatomic tag AT may include a solitary node (e.g., head, neck, chest, abdomen, upper extremity, lower extremity, et cetera) that is based on one or more non-hierarchical anatomic schemas, as opposed to the multi-level hierarchical anatomic schemas having at least one root node and leaf node as illustrated in FIG. 5 employed by the system 132. The artisan will thus understand that use of hierarchical anatomic schemas is merely exemplary and that a historical twin may likewise be identified using other anatomic schemas, including anatomic schemas each having a solitary node. Where non-hierarchical anatomic tags AT are used, the image evaluator 1558 may not be required to determine probabilities, e.g., of the primary and the secondary nodes as discussed above with respect to FIG. 2.

Because the archive 220 is arranged differently from archive 1520, components of the systems 132 and 1532 usable in creating these archives 220 and 1520 may likewise differ in relevant respects. As one example, the anatomy determiner 262 of system 132 may be configured to apply one or more hierarchical anatomic tags HT to the user image (UC) whereas the anatomy determiner 1562 of system 1532 may be configured to apply non-hierarchical anatomic tags AT to the user image (UC). Similarly, for instance, the AI arranger keys 252 and machine learning models 230 of system 132 may be configured in view of hierarchical anatomic schemas, whereas AI arranger keys 1552 and machine learning models 1530 may be configured in view of flat anatomic schemas.

Other variations are likewise contemplated. For example, while the anatomically arranged archive 220 is shown to have images that are multi-modal (e.g., X-rays, MRIs, CT scans, PET scans, et cetera), in embodiments, the anatomically arranged archive (e.g., archive 1520) may include anatomically arranged images of only a solitary modality (e.g., may include only X-rays, only MRIs, and so on). In other embodiments, multiple archives 1520 may be provided, each of which stores images associated with the same modality. Thus, for instance, a user case (UC) that is an X-ray of an arm of a user may be compared with images in an archive that only contains X-rays of patients. Similarly, a user case (UC) that is an MRI of a chest of a user may be compared with images in an archive that only contains MRI of patients.

Figure 16:
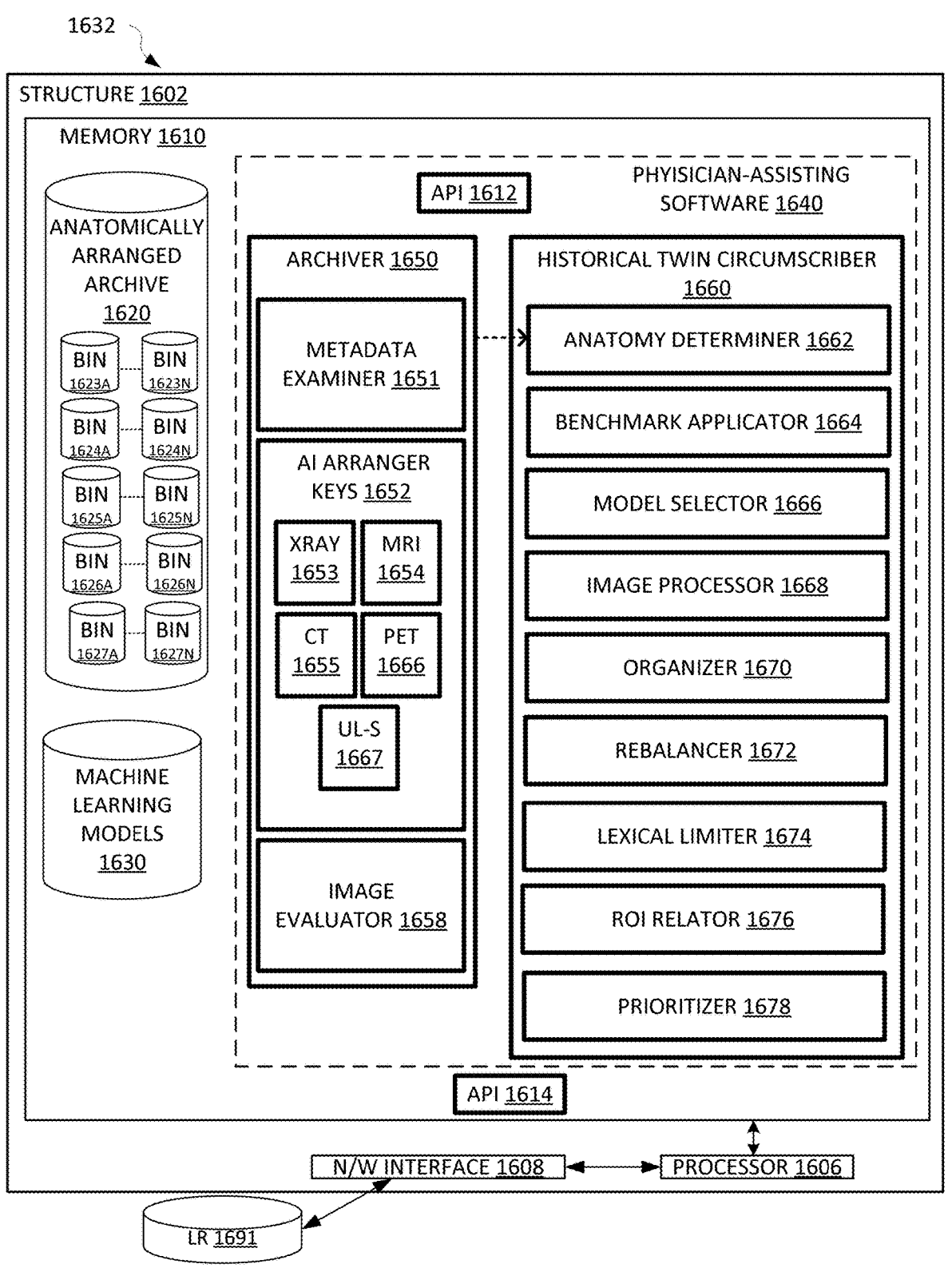
FIG. 16 schematically shows a physician-guided machine learning system, according to yet another embodiment.

FIG. 16 shows a machine learning system 1632 that may assist a physician in making a diagnosis by providing to the physician clinically relevant images and information based at least on benchmarks B set by the physician, according to still another embodiment. Aspects of the machine learning system 1632 in FIG. 16 may be identical or similar to those of the machine learning systems 132 in FIG. 2 and/or machine learning system 1532 in FIG. 15, except as noted herein or would be apparent or inherent. Further, those skilled in the art will appreciate that the system 132 (and thus the system 1632) may be modified in various ways, such as through incorporating all or part of any of the various described embodiments, for example. For uniformity and brevity, corresponding reference numbers may be used to indicate corresponding parts. For example, API 1612 of system 1632 may be generally identical to API 212 of system 132, processor 1606 may be generally identical to processor 206, rebalancer 1672 may be generally identical to rebalancer 272, and so on. The anatomically arranged archive 1620 may include medical images arranged using metadata tags MT and hierarchical anatomic tags HT as discussed with respect to machine learning system 132; alternately, the images in the archive 1620 may be arranged using metadata tags MT and non-hierarchical anatomic tags AT, as discussed with respect to machine learning system 1532.

The primary difference between the machine learning system 132 and the machine learning system 1632 may be that the machine learning system 1632, and specifically the historical twin circumscriber 1660 thereof, may include additional functionality as detailed herein. Specifically, the historical twin circumscriber 1660 of the machine learning system 1632 may include a lexical limiter 1674, a ROI relator 1676, and a prioritizer 1678, none of which were illustrated as being part of the system 132. The functionality of each of the lexical limiter 1674, the ROI relator 1676, and the prioritizer 1678 will be described in-turn.

As discussed above for the anatomically arranged archive 220, the anatomically arranged archive 1620 may likewise comprise, in addition to medical images, medical reports of the patients with whom the medical images are associated. Alternately, these medical reports may be stored in a different archive accessible to the software 1640, so long as the software 1640 may link a medical report in the different archive to a particular image or set of images of a patient in the anatomically arranged archive 1620. The medical reports may customarily include text entered by a medical professional reviewing the associated image(s) (e.g., a radiologist's description of an MRI, an ER physician's description of an X-ray, a urologist's description of an abnormality exhibited in a CT scan, et cetera). As described above, the machine learning system 132 may, at the back end, use natural language processing; for instance, once the historical twin search has been run, the organizer 270 of the machine learning system 132 may group historical twin results based on similarities in the various images together with similarities in the medical reports associated with these images. The machine learning system 1632, alternately or in addition, may use natural language processing at the front end to reduce the number of images that will need to be processed, including using image processing techniques.

In more detail, a medical professional reviewing the user image (UC) may, prior to selecting the region of interest or thereafter, provide a textual description of the feature(s) of interest (e.g., an abnormality) that is or will be encompassed by the region of interest (ROI). The graphical user interface associated with the machine learning system 1632 may allow for this description to be entered. For instance, a medical professional may describe the feature(s) of interest in a region of interest (ROI) in a user case (UC) as a "bubbly lytic lesion along the proximal diaphysis," a "slight increase in periaqueductal gray matter signal," a "partial tear in the Achilles 2 cm above the distal insertion," et cetera. The lexical limiter 1674, prior to any image processing of the user case (UC) (e.g., prior to ROI feature matching in steps 1114, 1115, 1116, 1118, and 1120 in method 1100), may first filter out from the archive 1620 those medical reports (and associated images) that do not include a match for the textual description of the user case (UC) provided by the medical professional. The medical reports and associated exams (including the images associated therewith) filtered out by the lexical limiter 1674 may be eliminated from further consideration, and the historical twin circumscriber 1660 may thereafter focus only on those medical reports (and their associated exams) that matched the description provided by the medical professional.

Minimizing the amount of time in which the historical twin results are generated may be important in view of the productivity requirements imposed on the medical professional.

The artisan understands that image processing large sets of images may be more computationally intensive, and thus, time consuming and/or expensive, relative to using natural language processing techniques on reports associated with such images.

The lexical limiter 1674 may be configured for natural language processing, including using techniques that are now known (e.g., as set forth herein) and/or developed in the future. In embodiments, therefore, the lexical limiter 1674 may employ such natural language processing techniques to filter out from the archive 1620 all those medical reports that do not include the medical professional's description of the user case (UC), and consequently, eliminate from further consideration all the medical images associated with the filtered out medical reports. The number of remaining images to be evaluated, using e.g., image processing techniques as in method 1100 in FIGS. 11A-11B, may be drastically reduced. In embodiments, the lexical limiter 1674 may reduce the number of images of the archive 1620 to be evaluated using the benchmarks B (see FIG. 8), i.e., using the binary criteria (BCR), weighted criteria (WCR), region of interest image processing, et cetera, to 10% or less (e.g., 1%, 5%, 7%, et cetera) of the total images in the archive 1620. Thus, a vast majority of the images in the anatomically arranged archive 1620 may be rejected out of hand by the lexical limiter 1674 prior to any computationally intensive image-processing-based comparisons of the user case (UC) and the images in the archive 1620.

In some embodiments, the medical professional may be able to adaptively configure the parameters of the natural language processing, based, e.g., on the user case (UC) at issue and the description thereof the medical professional is able to generate. In an embodiment, the natural language processing parameters (NLPP) may dictate whether and to what extent synonyms of words in a description provided by the medical professional are to be used in the search.

Figure 17:
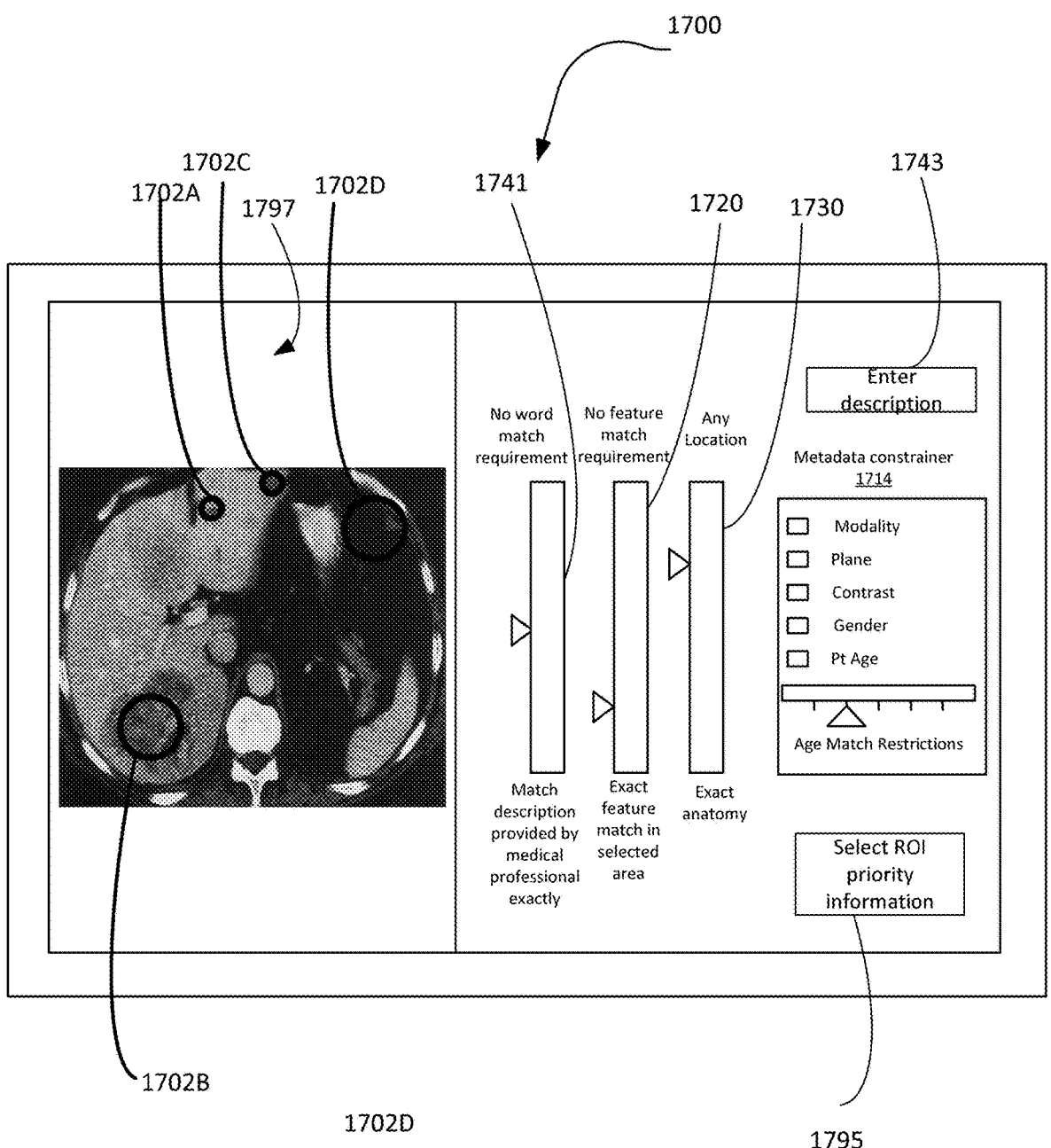
FIG. 17 shows an example graphical user interface of the physician-guided machine learning system of FIG. 16.

Focus is directed to FIG. 17, which shows an example graphical user interface 1700 usable by the medical professional to find a historical twin via the machine learning system 1632. Aspects of the GUI 1700 may be identical or similar to those of the GUI 1000 in FIG. 10, except as noted herein or would be apparent or inherent. Further, those skilled in the art will appreciate that the GUI 1000 (and thus the GUI 1700) may be modified in various ways, such as through incorporating all or part of any of the various described embodiments, for example. For uniformity and brevity, corresponding reference numbers may be used to indicate corresponding parts.

In much the same way as described for the graphical user interface 1000, the medical professional may use the home screen of the graphical user interface 1700 to select the benchmarks B for the search associated with the user image (UC), including the binary criteria (BCR) and the adaptively modifiable weighted criteria (WCR). The metadata constrainer 1714, ROI slider 1720, and anatomy slider 1730 of the GUI 1700 may generally correspond to the metadata constrainer 1014, ROI slider 1020, and anatomy slider 1030 of GUI 1000. One key difference between the GUI 1700 and the GUI 1000 may be that the GUI 1700 may further include a lexical slider 1741 and a text box 1743. The textual description of the feature(s) of interest may be entered by the medical professional in text box 1743. And, the medical professional may employ the lexical slider 1741 to set the parameters (NLPP) of the natural language search. The artisan will understand that use of the slider 1741 and the text box 1743 are merely exemplary and that the GUI 1700 may allow the medical professional to provide a textual description and select the natural language processing parameters (NLPP) in other ways (e.g., the medical professional may dictate the features of interest orally and use a knob to control the parameters of the natural language processing search). In some embodiments, the medical professional may employ the text box 1743 to craft Boolean searches (using, e.g., AND, OR, NOT operators, et cetera). In embodiments, the slider 1741 may be multi-faceted, e.g., have a certain number of fixed settable regions (such as match exactly, use equivalent words from any context, use equivalent words only in the medical context, use predefined ontologies, allowed contextual rearrangement, et cetera) and the medical professional may be able to select one or more of these facets as the natural language processing parameters.

In the illustrated example, where the medical professional sets the lexical slider 1741 to its strictest setting (at the bottom in this example), the lexical limiter 1674 may only return medical reports (and the images associated therewith) that match the textual description of the feature(s) of interest provided by the medical professional in text box 1743 exactly. Conversely, as the medical professional moves the lexical slider 1741 away from its strictest setting, the lexical limiter 1674 may return medical reports (and associated images) in addition to those that include text that matches the description of the medical professional exactly. For example, where the lexical slider 1741 is set towards the middle, the lexical limiter 1674 may return medical reports (and associated images) that include only some of the words or descriptors in the medical professional's description and/or include well-known alternatives of all or some of the words or descriptors in the medical professional's description. As the lexical slider 1741 is moved further away from its strictest setting, the lexical limiter 1674 may include in its results those medical reports (and associated images) that comprise any word in the medical professional's description or a synonym (or a poecilonym, a metonym, et cetera) thereof. A "synonym" of a term, as the word "synonym" is used herein, refers to two terms each of which may be used by a medical professional to describe the same idea or thing (e.g., renal and kidney, nasal and nose, pole and half, distal and anterior, et cetera).

The ability to employ natural language processing techniques to search for clauses and synonyms of one or more words that make up those clauses may be particularly useful in identifying relevant results that include feature(s) which different medical professionals connote in different ways. In embodiments, the structure 1602 may include or the lexical limiter 1674 may access over a network (e.g., the web using network interface 1608) lexical resources 1691 (see FIG.

16). The lexical resources 1691 may comprise medical dictionaries (e.g., Mosby's, Webster's, et cetera) and thesauri to allow the lexical limiter 1674 to determine one or more synonyms of a term. Related words may also manually be introduced. In embodiments, the lexical resources 1691 may include translational dictionaries, so that relevant results reviewed by medical professionals in other languages may be considered.

In embodiments where natural language processing parameters (NLPP) are selectively alterable by the medical professional (using, e.g., the lexical slider 1741), the percentage of medical reports (and associated images) filtered out by the lexical limiter 1674 and disregarded from further consideration may depend on the textual description and the search parameters selected by the medical professional. For instance, where the lexical slider 1741 is set to its strictest setting, and the medical professional's description of the abnormality includes words that are not exceedingly common, a vast majority (e.g., 99% or more) of the reports and associated images in the anatomically arranged archive 1620 may be filtered out and disregarded in the subsequent process steps carried out during the search for the historical twin; additional images may be filtered via use of the binary criteria (BCR), and thus, only a very small subset of images (e.g., under 1%) in the archive 1620 may undergo image processing to locate the historical twin. As the lexical slider 1741 is moved away from its strictest setting, the number of reports and associated images that are filtered out may decrease. For example, where the lexical slider 1741 is set towards the middle, and depending on the words in the description, the lexical limiter 1674 may filter out 90% of the medical reports and records from further consideration, and a relatively larger number of medical images may ultimately be processed using image processing techniques when locating the historical twin.

To ensure that the verbiage used by the medical professional and the settings for the lexical limiter 1674 chosen by the medical professional are appropriate (e.g., will not result in an unduly small or unduly large number of medical reports), the lexical limiter 1674 may at the outset indicate the number of medical reports that will be turned up by the lexical limiter 1674 in response to the medical professional's query. Such feedback may help the medical professional better tailor the input query if needed. For example, where the lexical limiter 1674 indicates that hundreds of thousands of medical reports match the input criteria, the medical professional may change same (e.g., use different verbiage and/or use a stricter setting for the lexical slider 1741) so that a more suitable number of results is unearthed.

For example, assume that the medical professional describes the abnormality in the user case (UC) as: "punctate cortical infarct." The lexical limiter 1674 may indicate that this search yields an unduly large number (e.g., thousands) of medical reports. The medical professional may therefore narrow the search string to instead provide: "punctate cortical infarct in the left parietal lobe," to obtain a suitable number of results. Such functionality may help ensure that the medical professional is on the right track and that much time is not wasted generating and/or sifting through an unsuitable number of results.

The lexical limiter 1674 and the lexical slider 1741 will now be illustrated using an example. Consider, for example, that the medical professional describes the user case (UC) (and specifically the region of the user image in which the medical professional is interested) by typing, using the GUI 1700 and the text box 1743, the following clause: "renal cyst in the left lower pole." Assume that the medical professional sets the lexical slider 1741 at the strictest setting. In such case, the lexical limiter 1674 may query the medical reports associated with the images in the anatomically arranged archive 1620 to find this exact clause, and filter out all the medical reports (and associated images) that do not include this clause. The images subsequently considered by the historical twin circumscriber 1660 may therefore be limited to those that have associated therewith the particular description employed by the medical professional.

Assume now that the medical professional sets the lexical slider 1741 closer to the top (i.e., towards the "loosest" or most inclusive setting). In this case, the lexical limiter 1674 may first determine synonyms of at least some of the terms in the clause in question, so that the medical records (and associated images) having the exact terms set forth by the medical professional and their synonyms may each be located for further review. For instance, the lexical limiter 1674 may determine that "kidney" is a synonym for "renal," that "half" and "pole" are synonymous, that a "cyst" may also be referred to as a "blister," "sac," or "mass," et cetera. Thus, for example, the lexical limiter 1674 may keep for further evaluation (e.g., using image processing) a medical report (and associated image(s)) that includes the clause: "thin-walled mass in lower half of left kidney."

As another example, where the medical professional describes the user case (UC), and specifically the region of the user image in which the medical professional is interested, using the clause: "discontinuous, peripherally enhancing lesion in the right lobe of the liver" may, based on the settings chosen, retain for further evaluation a medical report (and associated image(s)) that includes the clause: "right hepatic lobe contains a heterogeneous rim enhancing nodule."

In certain applications, the lexical resources 1691 may comprise resources based on predefined ontologies and their controlled vocabularies (e.g., RadLex, which is focused on the radiology field), as such may further aid in efficient filtering by the lexical limiter 1674. In some embodiments, a medical professional may be able to employ the natural language processing parameters (NLPP) to limit the natural language processing carried out by the lexical limiter 1674 to a particular domain of interest; for example, the medical professional may be able to focus the lexical limiter processing to concepts applicable to thoracic cases where the interest of the medical professional in the user case (UC) is limited to the thoracic domain.

FIG. 18 is a flowchart illustrating an example method 1800 of using the machine learning system 1632, and particularly, the lexical limiter 1674 thereof. The method 1800 may start at step 1802, and at step 1804, the medical professional may enter a textual description of the feature(s) of interest in the user case (UC) via the GUI 1700. For example, the medical professional may enter the textual description in the text box 1743.

At step 1806, the medical professional may set at least one natural language processing parameters (NLPP) for the lexical limiter 1674. For example, as discussed above, the medical professional may set the lexical slider 1741 so as to ensure that synonyms of words within the textual description provided by the medical professional are considered. As noted, the medical professional may alternately or additionally set the natural language parameters in other ways. For instance, the medical professional may limit the searching by the lexical limiter 1674 to particular domains or areas of interest, introduce Boolean operators in the search, et cetera.

At step 1808, the lexical limiter 1674 may filter out medical reports in the archive 1620 based on natural language processing to create a relevant set (RS) of medical images. The relevant set (RS) of medical images may be those images in the archive 1620 which have associated therewith a medical report that was identified by the lexical limiter 1674 because it met the criteria set forth by the medical professional. Medical images outside the relevant set (RS), i.e., medical images associated with the medical reports filtered out by the lexical limiter 1674, may be eliminated from further consideration by the historical twin circumscriber 1660. The medical images associated with medical reports that are filtered out by the lexical limiter 1674 (i.e., medical images outside the relevant set (RS)) may account for a vast majority (e.g., about 75% to about 99%) of images in the archive 1620. This step may in applications be useful from an efficiency standpoint because a single medical report may have associated therewith a plurality (e.g., ten, hundred, or even a thousand or more) of images and each of these plurality of images may be filtered out by filtering out the medical report associated therewith using the natural language processing techniques described herein.

At step 1810, the historical twin circumscriber 1660 may evaluate images in the relevant set (RS), including using image processing techniques, to find a historical twin(s). For example, as discussed with respect to the method 1100 in FIGS. 11A-11B, the historical twin circumscriber 1660 may create a first reduced set (FRS) (now from the relevant set (RS) as opposed to from the entire archive 1620) using the benchmark applicator 1664, create a second reduced set (SRS) from the first reduced set (FRS) using the anatomy determiner 1662, create an optimal set (OS) from the second reduced set (SRS) based on the weight given by the medical professional to anatomy via the anatomy slider 1730, and then use the image processor 1668 to identify the historical twin from images within the optimal set (OS).

While FIG. 18 shows that natural language processing is used to limit the data set subsequently evaluated using the method 1100 (i.e., that the natural language processing is carried out at the front end), in some embodiments, the natural language processing and the method 1100 may run independently (e.g., in tandem). That is, in embodiments, parallel searches to locate the historical twin may be run, one that focuses on the textual description and natural language processing techniques, and the other that focuses on the binary criteria, weighted criteria, anatomy, region of interest (ROI), et cetera, as shown in FIGS. 11A-11B. In these embodiments, preference may be given in the results displayed to the medical professional to those images that are independently identified using each of the two disparate search methodologies. In other embodiments still, the natural language search may be run only at the back end, to further limit the results identified by other means (e.g., using the method 1100). In some embodiments, a medical professional may be allowed to opt out of natural language processing or anatomic matching entirely depending upon the context of relative strength of one or the other approach. For instance, where the abnormality of interest is a bubbly lytic lesion in the metaphysis of the tibia of a skeletally immature patient, natural processing techniques may be sufficient to enable the medical professional to find the historical twin.

As describe above with respect to the machine learning system 132, the medical professional may select the benchmarks B based on the user case (UC) in question, or alternately, the machine learning system 132 may select one or more benchmarks based on presets and/or best practices. The same concepts may be applicable to the machine learning system 1632. For instance, the historical twin circumscriber 1660 may automatically restrict the age for a descriptor that includes osteopenia to be greater than forty years of age because this condition is rarely seen in patients that are under this age. As another example, where the medical professional describes the abnormality as a lytic lesion, the historical twin circumscriber 1660 may automatically restrict the anatomy of the search set to be strictly restricted to bones.

Focus is directed back to FIG. 17. Another key difference between the interface 1000 (FIG. 10) and the interface 1700 (FIG. 17) may be that the interface 1700 may further include an interacter 1795 that allows the medical professional to interact with the prioritizer 1678 (see FIG. 16). As discussed herein, the medical professional may be allowed to select more than one region of interest (ROI) in a medical image via the interface 1700, and the prioritizer 1678 may allow for one or more of these regions of interest (ROI) to be prioritized over another one or more of these regions of interest (ROI) based on input provided by a medical professional.

Assume, for example, that the medical professional selects a region of interest (ROI) 1702A in the user case (UC), image 1797 in the FIG. 17 example, because the region 1702A includes a clinically relevant abnormality (say, a lesion). Assume that the image 1797 exhibits additional lesions that are ornamentally comparable (e.g., identical or visually similar) to the lesion in ROI 1702A. These additional lesions may inform the clinical diagnosis of the user case (UC). For example, a lytic bone lesion may have a different diagnosis if it is a solitary lesion versus if there are multiple such lesions. To account for the possibility that the user case (UC) may include a plurality of comparable abnormalities (e.g., a plurality of similar lesions) that are associated with each other, the interface 1700 may allow the medical professional to select more than one region of interest (ROI) in a solitary image. For example, as shown in FIG. 17, the medical professional has demarcated four regions of interest 1702A, 1702B, 1702C, and 1702D on the same medical image 1797 because each of these regions of interest encompasses an ornamentally comparable region and the clinical diagnosis may be informed by the association of these regions in the same exam. Additionally, by having multiple ROIs to utilize, the historical twin circumscriber 1660 will be able to more readily eliminate cases that have ROI features matching all the identified regions (if designated by the ROI slider 1720).

In some embodiments, e.g., in case where the medical professional fails to identify on the image (e.g., image 1797) additional regions of interest (ROIs) encompassing abnormalities that are potentially associated with the abnormality in the region of interest (ROI) selected by the medical professional, the ROI relator 1676 may highlight these additional potential regions of interest (PROI) and inquire whether the medical professional wishes for these additional potential regions of interest (PROIs) to be considered as well. For example, where the medical professional identifies a lesion with calcification on the user image (UC), the ROI relator 1676 may process the user image (UC) to determine whether the user image (UC) contains other lesions that are comparable to the lesion identified by the medical professional, and if so, highlight these other lesions for the medical professional as potential regions of interest (PROIs). The ROI relator 1676 may identify the potential regions of interest (PROI) by, e.g., extracting features in the region of interest (ROI) and determining whether comparable features are present elsewhere in the image. The medical professional may approve one or more of the potential regions of interest (PROI) as a region of interest (ROI) to be considered during the search for the historical twin. Where, for example, the medical professional selects a region of interest (ROI) and the ROI relator 1676 identifies another potential region of interest (PROI) that is ultimately approved by the medical professional, the historical twin circumscriber 1660 may emphasize in the results those images that have two of the type of lesion identified by the medical professional in the two regions of interest (ROIs). Similarly, where the medical professional selects three disparate and spaced apart regions of interest (ROI) on a user image, each of which contain a nodule that may be associated with the other two nodules, the historical twin circumscriber 1660 may emphasize in the results those images that have three of the type of lesion identified by the medical professional.

The artisan will understand that it may be preferable to select a plurality of regions of interest each of which includes an associated abnormality (e.g., a calcified nodule), as opposed to selecting one large region of interest (ROI) that encompasses these plurality of abnormalities (e.g., a larger region of interest (ROI) that includes the multiple calcified nodules). The latter approach of selecting a solitary region of interest (ROI) that encompasses the plurality of abnormalities in the image may result in an unduly large region of interest (ROI) that also include features not of interest to the medical professional, which may be undesirable from an optimal set generation standpoint.

In embodiments, the multiple regions of interest (ROIs) need not be related to each other. For example, a medical professional may select two regions of interest (ROIs) that each include a calcified nodule and select another region of interest (ROI) that includes a nodule that is not calcified, or an unrelated abnormality (e.g., a tear, an inflammation, et cetera).

As discussed, where the medical professional selects a region of interest (ROI) that includes a particular abnormality, say a lesion, identification of other similar abnormalities (e.g., other similar lesions) in the user case (UC) may be of importance in locating a historical twin. In embodiments, the size of the abnormality, e.g., a lesion, may also be clinically relevant. For instance, a 3 cm mass with the same characteristics as a 5 mm mass may have a completely different diagnosis where these two masses appear in the lung, whereas the size difference of these two masses may not be clinically dispositive where these lesions appear in the brain. Thus, both the number and size of the abnormality may be important features to narrow a data set to increase diagnostic relevancy of the search for the historical twin as described herein. In embodiments, the ROI relator 1676 may indicate the size of the abnormality associated with each region of interest (ROI) proposed by the ROI relator 1676, so the medical professional may have the opportunity to limit the search to those regions of interest (ROI) that include abnormalities that are relevant to the clinical question being asked. This may differentiate from currently available AI solutions where results are presented without an opportunity to refine the method or seed algorithm used to locate the search results.

In embodiments, the medical professional may be allowed to prioritize one or more region of interest (ROI) over one or more other region(s) of interest (ROI) by using the interacter 1795 for the prioritizer 1678. Consider, for example, the four regions of interest 1702A, 1702B, 1702C, and 1702D. Assume that the medical professional considers the regions of interest 1702A and 1702B to be of critical clinical importance, the region of interest 1702C to be of less clinical importance, and the region of interest 1702D to be of less diagnostic relevance still. The prioritizer 1678 may allow the medical professional to prioritize region of interests 1702A and 1702B over region of interest 1702C, and prioritize these regions of interest over region of interest 1702D. The medical professional may likewise be able to employ the interacter 1795 to indicate that images that match only on the region of interest 1702C or 1702D, or images that match only on one of the regions of interest 1702A and 1702B, are to be disregarded, In this example, the historical twin circumscriber 1660 may emphasize the results that match the user case (UC) on all four regions of interest 1702A, 1702B, 1702C, and 1702D. The historical twin circumscriber 1660 may include in the results those images that meet the user-supplied matching criteria for a subset of these regions of interest, e.g., match on regions of interest 1702A, 1702B, and 1702C (or 1702D). However, images that match only region of interest 1702C and/or 1702D may be disregarded or given reduced importance in line with the medical professional's prioritization of regions of interest 1702A and 1702B together. In embodiments, a separate slider or other means may be provided to allow the medical professional to prioritize a given number of a particular abnormality (e.g., a medical professional may be able to use a slider, text box, knob, et cetera, to indicate that all relevant results will have at least two of the types of lesions in a particular region of interest (ROI)).

FIG. 19 shows a method 1900 of using the ROI relator 1676 and the prioritizer 1678 of the machine learning system 1632. The method begins at step 1902. At step 1904, the medical professional identifies a region of interest (ROI) in the user case (UC). As discussed, the medical professional may select a solitary region of interest, a plurality of regions of interest that includes abnormalities related or likely to be related to each other, or a plurality of regions of interest at least one of which includes an abnormality that is not associated with the abnormality in another region of interest.

At step 1906, the ROI relator 1676 may process the user case (UC) using image processing techniques and identify potential regions of interest (PROIs). For example, where the region of interest (ROI) selected by the medical professional includes a calcified lesion, the ROI relator 1676 may identify one or more other calcified lesions in the image as potential regions of interest (PROIs) for the medical professional's consideration. The ROI relator 1676 may, in embodiments, provide dimensional information regarding the abnormality in the region(s) of interest (ROI) and the potential region(s) of interest (PROI), e.g., indicate that the lesion in the region of interest (ROI) is 2 cm whereas the lesion in a PROI is 5 mm.

Figure 20:
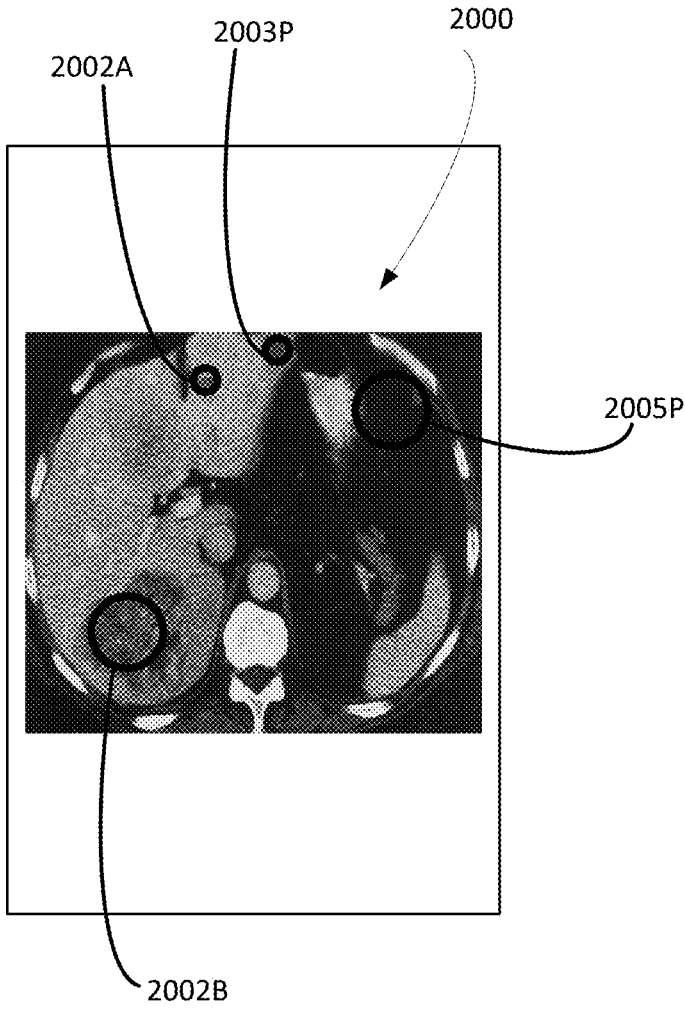
FIG. 20 shows potential regions of interest identified on a user image by the physician-guided machine learning system of FIG. 16.

FIG. 20 shows an example potential region of interest (PROI). Specifically, FIG. 20 shows a user case (UC) 2000 and regions of interest (ROI) 2002A and 2002B identified thereon by a medical professional. Assume that the region of interest (ROI) 2002A includes a lesion of a first size and ROI 2002B includes a lesion of a second size. In this example, the ROI relator 1676 has identified potential region of interest (PROI) 2003P because it contains a lesion that is ornamentally comparable to the lesion in ROI 2002A (e.g., PROI 2003P may include a lesion whose size is within a given percentage of the size of the lesion in ROI 200A), and has identified PROI 2005P because it contains a lesion that is ornamentally comparable to the lesion in 2002B.

Returning to FIG. 19, at step 1908, the medical professional may approve one or more potential regions of interest (PROIs) as an additional region of interest (ROI). The medical professional may approve as a region of interest (ROI) only a subset of the potential regions of interest (PROIs) identified by the ROI relator 1676. For example, the medical professional may discard a potential region of interest (PROI) including a lesion where the medical professional determines this lesion is not related to the lesion in the region of interest (ROI) identified by the medical professional. Or, the medical professional may discard all the potential region of interest (PROI). In some embodiments, the act of eliminating PROIs at this step may be used to exclude ROIs that are better matches for the eliminated PROIs than the approved ROIs.

At step 1910, the medical professional may prioritize one or more regions of interest (ROIs) and/or one or more groupings of regions of interest (ROI) over one or more other regions of interest (ROIs) or groupings thereof. For example, where the user case (UC) includes five regions of interest, the medical professional may prioritize the first region of interest over the second region of interest and so on. The priorities set by the medical professional may be taken into account by the historical twin circumscriber 1660 in searching for the historical twin. In some embodiments, the one or more regions of interest (ROIs) prioritized by the medical professional may be considered at the back end (e.g., a first pass of the search results may first be generated without taking into account the ROI priorities and the results may be filtered in view of these priorities). In other embodiments, the ROI priorities set by the medical professional may be used as inputs prior to ROI-based image processing, e.g., in the method 1100.

At step 1912, the historical twin circumscriber 1640 may search for images of other patients that meet the criteria set forth by the medical professional, to allow for the identification of the historical twin. For example, as discussed with respect to the method 1100, the historical twin circumscriber 1640 may locate candidates for historical twins based on the binary criteria, weighted criteria, the region of interest, weights given the medical professional to anatomy and region of interest features, and so on. As discussed, the historical twin circumscriber 1660 may take into account more than one region of interest (ROI) and, based on the medical professional's input, prioritize one or more regions of interest (ROIs) over one or more other regions of interest (ROIs). In this way, the machine learning system 1632 may allow the medical professional to employ additional techniques to locate a historical twin relative to the machine learning system 132.

Thus, as has been described, the physician-assisting software 240, 1540, and 1640 may, based on criteria provided and/or approved by the medical professional, locate medically relevant images of other patients, and assist the physician in locating a historical twin so that the physician can make a diagnosis of the patient at issue informed by the diagnosis of the historical twin.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure. For example, while the systems and methods have been described primarily with an eye towards aiding the physician in making a diagnosis, the techniques may likewise be usable as educational tools or towards optimizing patient treatment (e.g., treatment of patients with small cell cancer with a hydro-pneumothorax and survival of historical twin patients is noted to be better when receiving a particular treatment regimen).

It will be understood that certain features and subcombinations are of utility and may be employed without reference to other features and subcombinations and are contemplated within the scope of the claims. Not all steps listed in the various figures need be carried out in the specific order described.

The disclosure claimed is:

1. A computer-implemented method of evaluating a user image of a patient to enable identification of a historical twin of said patient, comprising:

(a) processing a plurality of medical images to determine an anatomic characterization of each of said plurality of medical images;

(b) organizing each of said plurality of medical images in an archive using said determined anatomic characterization and metadata;

(c) displaying said user image using a graphical user interface;

(d) receiving from a medical professional, in connection with said user image and via said graphical user interface, each of: (i) a region of interest; (ii) a medical-professional-entered textual description associated with said region of interest; (iii) a natural language search parameter; (iv) selections for binary criteria; and (v) weights of weighable criteria, including a weight to be given to each of: (v)(a) an anatomical location of said region of interest; and (v)(b) features of said region of interest;

(e) using a natural language search configured using said natural language search parameter to create a relevant set of medical images from said archive;

(f) creating an optimal set of medical images from said relevant set of medical images by discarding medical images from said relevant set of medical images based on said selections for binary criteria, said weight of said anatomical location of said region of interest, and said medical-professional-entered textual description; and (g) image processing medical images in said optimal set using said weight of said features of said region of interest to create medical image results;

wherein, said relevant set comprises less than ten percent of said plurality of medical images in said archive.

2. The method of claim 1 further comprising indicating for said medical professional on said graphical user interface a potential region of interest.

3. The method of claim 1, wherein said region of interest comprises at least two disparate regions of interest.

4. The method of claim 1, wherein said graphical user interface is configured to allow said medical professional to prioritize one of said at least two disparate regions of interest.

5. The method of claim 1, wherein said natural language search parameter dictates consideration of a synonym in said natural language search.

6. The method of claim 1, wherein said graphical user interface comprises a multi-faceted slider for setting said natural language search parameter.

7. The method of claim 1, wherein said anatomic characterization is a hierarchical characterization.

8. The method of claim 1, wherein said anatomic characterization is non-hierarchical.

9. A computer-implemented method of evaluating a user image of a patient to enable identification of a historical twin of said patient, comprising:

(a) organizing a plurality of medical images in an archive;

(b) displaying said user image using a graphical user interface;

(c) receiving from a medical professional, in connection with said user image and via said graphical user interface, each of: (i) a plurality of regions of interest; (ii) a medical-professional-entered textual description associated with at least one of said plurality of regions of interest; (iii) selections for binary criteria; (iv) priority information for prioritizing at least one of said plurality of regions of interest; and (v) weights of weighable criteria, including a weight to be given to each of: (v)(a) an anatomical location of at least one of said plurality of regions of interest; and (v)(b) features of at least one of said plurality of regions of interest;

(d) using a natural language search to create a relevant set of medical images from said archive;

(e) creating an optimal set of medical images from said relevant set of medical images by discarding medical images from said relevant set of medical images based on said selections for binary criteria, said medical-professional-entered textual description, and said weight of said anatomical location of at least one of said plurality of regions of interest; and (f) image processing medical images in said optimal set using said weight of said features of at least one of said regions of interest to create medical image results;

wherein, said relevant set comprises less than ten percent of said plurality of medical images in said archive.

10. The method of claim 9, further comprising obtaining from said medical professional a natural language search parameter.

11. The method of claim 10, wherein said natural language search parameter dictates consideration of a synonym in said natural language search.

12. The method of claim 10, wherein said natural language search parameter limits said natural language search to a body part.

13. The method of claim 9, further comprising presenting to said medical professional a potential region of interest derived from an ornamental similarity between said potential region of interest and at least one of said plurality of regions of interest identified by said medical professional.

14. The method of claim 13, wherein said potential region of interest is determined using image processing.

15. A computer-implemented method of evaluating a user image of a patient to enable identification of a historical twin of said patient, comprising:

(a) organizing a plurality of medical images in an archive;

(b) displaying said user image using a graphical user interface;

(c) receiving from a medical professional, in connection with said user image and via said graphical user interface, each of: (i) a region of interest; (ii) a medical-professional-entered textual description; (iii) selections for binary criteria; and (iv) weights of weighable criteria, including a weight to be given to each of: (iv)(a) an anatomical location of said region of interest; and (iv)(b) features of said region of interest;

(d) using a natural language search to create a relevant set of medical images from said archive;

(e) creating an optimal set of medical images from said relevant set of medical images by discarding medical images from said relevant set of medical images based at least on said selections for binary criteria and said medical-professional-entered textual description; and (f) image processing medical images in said optimal set using said weight of said features of said region of interest to create medical image results;

wherein, said relevant set comprises less than ten percent of said plurality of medical images in said archive.

16. The method of claim 15, further comprising presenting on the graphical user interface a potential region of interest.

17. The method of claim 16, further comprising selecting said potential region of interest as an additional region of interest.

18. The method of claim 15, wherein a number of images in said optimal set is less than ten percent of a number of images in said relevant set.

19. The method of claim 15, further comprising providing a lexical slider for setting a natural language search parameter.

20. The method of claim 15, wherein said plurality of medical images are multi-modal.

* * * * *